United States Patent
Rocheleau et al.

(10) Patent No.: US 6,641,525 B2
(45) Date of Patent: Nov. 4, 2003

(54) SLING ASSEMBLY WITH SECURE AND CONVENIENT ATTACHMENT

(75) Inventors: Gary A. Rocheleau, Maple Grove, MN (US); Johann J. Neisz, Coon Rapids, MN (US); Gary J. Nachreiner, Mound, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 09/990,108

(22) Filed: Nov. 21, 2001

(65) Prior Publication Data

US 2002/0151762 A1 Oct. 17, 2002

Related U.S. Application Data

(63) Continuation-in-part of application No. 10/005,837, filed on Nov. 9, 2001, and a continuation-in-part of application No. 09/917,443, filed on Jul. 27, 2001, and a continuation-in-part of application No. 09/917,562, filed on Jul. 27, 2001.

(60) Provisional application No. 60/269,829, filed on Feb. 20, 2001, provisional application No. 60/281,350, filed on Apr. 4, 2001, provisional application No. 60/295,068, filed on Jun. 1, 2001, provisional application No. 60/306,915, filed on Jul. 20, 2001, and provisional application No. 60/332,330, filed on Nov. 20, 2001.

(51) Int. Cl.$^7$ .................................................. A61F 2/00
(52) U.S. Cl. ..................................................... 600/30
(58) Field of Search .............................. 600/29–31, 37; 606/119, 148, 222–225; 128/DIG. 25

(56) References Cited

U.S. PATENT DOCUMENTS

| | | | |
|---|---|---|---|
| 2,738,790 | A | 3/1956 | Todt et al. |
| 3,054,406 | A | 9/1962 | Usher |
| 3,124,136 | A | 3/1964 | Usher |
| 3,182,662 | A | 5/1965 | Shirodkar |
| 3,311,110 | A | 3/1967 | Singerman et al. |
| 3,384,073 | A | 5/1968 | Van winkle, Jr. |
| 3,384,074 | A | 5/1968 | Van winkle, Jr. |
| 3,472,232 | A | 10/1969 | Earl |

(List continued on next page.)

FOREIGN PATENT DOCUMENTS

| | | |
|---|---|---|
| DE | 2305815 | 2/1973 |
| DE | 4220283 C2 | 5/1994 |
| EP | 0470308 A1 | 2/1992 |

(List continued on next page.)

OTHER PUBLICATIONS

Beck, Peter R. et al., Treatment of Urinary Stress Incontinence With Anterior Colporrhaphy, Obstetrics and Gynecology, Vol 59 (No. 3), pp. 269–274 (Mar. 1982).

Benderev, Theodore V., MD, A Modified Percutaneous Outpatient Bladder Neck Suspension System, Journal of Urology, vol. 152, pp. 2316–2320 (Dec. 1994).

(List continued on next page.)

*Primary Examiner*—Samuel G. Gilbert
(74) *Attorney, Agent, or Firm*—Jeffrey J. Hohenshell

(57) ABSTRACT

Surgical articles that are conveniently and securely coupled are disclosed. Improved surgical procedures are also disclosed.

15 Claims, 15 Drawing Sheets

U.S. PATENT DOCUMENTS

| | | |
|---|---|---|
| 3,763,860 A | 10/1973 | Clarke |
| 3,789,828 A | 2/1974 | Schulte |
| 3,924,633 A | 12/1975 | Cook et al. |
| 3,995,619 A | 12/1976 | Glatzer |
| 4,037,603 A | 7/1977 | Wendorff |
| 4,172,458 A | 10/1979 | Pereyra |
| 4,235,238 A | 11/1980 | Ogiu et al. |
| 4,246,660 A | 1/1981 | Wevers |
| 4,441,497 A | 4/1984 | Paudler |
| 4,509,516 A | 4/1985 | Richmond |
| 4,775,380 A | 10/1988 | Seedhom et al. |
| 4,857,041 A | 8/1989 | Annis et al. |
| 4,865,031 A | 9/1989 | O'Keeffe |
| 4,932,962 A | 6/1990 | Yoon et al. |
| 4,938,760 A | 7/1990 | Burton et al. |
| 4,969,892 A | 11/1990 | Burton et al. |
| 5,012,822 A | 5/1991 | Schwarz |
| 5,013,292 A | 5/1991 | Lemay |
| 5,019,032 A | 5/1991 | Robertson |
| 5,032,508 A | 7/1991 | Naughton et al. |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,209,756 A | 5/1993 | Seedhom et al. |
| 5,250,033 A | 10/1993 | Evans et al. |
| 5,256,133 A | 10/1993 | Spitz |
| 5,281,237 A | 1/1994 | Gimpelson |
| 5,328,077 A | 7/1994 | Lou |
| 5,337,736 A | 8/1994 | Reddy |
| 5,362,294 A | 11/1994 | Seitzinger |
| 5,368,595 A | 11/1994 | Lewis |
| 5,383,904 A | 1/1995 | Totakura et al. |
| 5,403,328 A | 4/1995 | Shallman |
| 5,413,598 A | 5/1995 | Moreland |
| 5,439,467 A | 8/1995 | Benderev et al. |
| 5,520,700 A | 5/1996 | Beyar et al. |
| 5,544,664 A | 8/1996 | Benderev et al. |
| 5,562,689 A | 10/1996 | Green et al. |
| 5,591,163 A | 1/1997 | Thompson |
| 5,611,515 A | 3/1997 | Benderev et al. |
| 5,628,756 A | 5/1997 | Barker, Jr. et al. |
| 5,807,403 A | 9/1998 | Beyar et al. |
| 5,836,314 A | 11/1998 | Benderev et al. |
| 5,836,315 A | 11/1998 | Benderev et al. |
| 5,842,478 A | 12/1998 | Benderev et al. |
| 5,860,425 A | 1/1999 | Benderev et al. |
| 5,899,909 A | 5/1999 | Claren et al. |
| 5,934,283 A | 8/1999 | Willem et al. |
| 5,935,122 A | 8/1999 | Fourkas et al. |
| 5,944,732 A | 8/1999 | Raulerson et al. |
| 5,945,122 A | 8/1999 | Abra et al. |
| 5,972,000 A | 10/1999 | Beyar et al. |
| 5,997,554 A | 12/1999 | Thompson |
| 6,010,447 A | 1/2000 | Kardjian |
| 6,030,393 A | 2/2000 | Corlew |
| 6,039,686 A | 3/2000 | Kovac |
| 6,042,534 A | 3/2000 | Gellman et al. |
| 6,042,536 A | 3/2000 | Tihon et al. |
| 6,053,935 A | 4/2000 | Brenneman et al. |
| 6,068,591 A | 5/2000 | Bruckner et al. |
| 6,071,290 A | 6/2000 | Compton |
| 6,106,545 A | 8/2000 | Egan |
| 6,110,101 A | 8/2000 | Tihon et al. |
| 6,117,067 A | 9/2000 | Gil-Vernet |
| 6,273,852 B1 | 8/2001 | Lehe et al. |
| 6,302,840 B1 | 10/2001 | Benderev |
| 6,322,492 B1 | 11/2001 | Kovac |
| 6,328,686 B1 | 12/2001 | Kovac |
| 6,328,744 B1 | 12/2001 | Harari et al. |
| 6,334,446 B1 | 1/2002 | Beyar |
| 6,382,214 B1 | 5/2002 | Raz et al. |
| 6,406,423 B1 | 6/2002 | Scetbon |
| 6,423,080 B1 | 7/2002 | Gellman et al. |
| 6,478,727 B2 | 11/2002 | Scetbon |
| 6,502,578 B2 | 1/2003 | Raz et al. |
| 6,530,943 B1 | 3/2003 | Hoepffner et al. |
| 2001/0018549 A1 | 8/2001 | Scetbon |
| 2001/0049467 A1 | 12/2001 | Lehe et al. |
| 2001/0053916 A1 | 12/2001 | Rioux |
| 2002/0028980 A1 | 3/2002 | Thierfelder et al. |
| 2002/0055748 A1 | 5/2002 | Gellman et al. |
| 2002/0058959 A1 | 5/2002 | Gellman |
| 2002/0068948 A1 | 6/2002 | Stormby et al. |
| 2002/0077526 A1 | 6/2002 | Kammerer et al. |
| 2002/0091373 A1 | 7/2002 | Berger |
| 2002/0099260 A1 | 7/2002 | Suslian et al. |
| 2002/0107525 A1 | 8/2002 | Harari et al. |
| 2002/0115906 A1 | 8/2002 | Miller |
| 2002/0128670 A1 | 9/2002 | Ulmsten et al. |
| 2002/0138025 A1 | 9/2002 | Gellman et al. |
| 2002/0151909 A1 | 10/2002 | Gellman et al. |
| 2002/0151910 A1 | 10/2002 | Gellman et al. |
| 2002/0156487 A1 | 10/2002 | Gellman et al. |
| 2002/0156488 A1 | 10/2002 | Gellman et al. |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023137 A1 | 1/2003 | Gellman et al. |
| 2003/0023138 A1 | 1/2003 | Luscombe |
| 2003/0036676 A1 | 2/2003 | Scetbon |
| 2003/0045774 A1 | 3/2003 | Staskin et al. |
| 2003/0050530 A1 | 3/2003 | Neisz et al. |

FOREIGN PATENT DOCUMENTS

| | | |
|---|---|---|
| EP | 0 650 703 A1 | 6/1994 |
| EP | 0 643 945 A2 | 7/1994 |
| EP | 1093758 A1 | 10/2000 |
| SU | 1225547 A1 | 4/1986 |
| WO | 93/17635 | 3/1993 |
| WO | WO 98/35616 A1 | 8/1998 |
| WO | WO 00/64370 A1 | 2/2000 |
| WO | 00/18319 | 4/2000 |
| WO | 00/57812 | 10/2000 |
| WO | 00/74594 A1 | 12/2000 |
| WO | 00/74613 A1 | 12/2000 |
| WO | 00/74633 A2 | 12/2000 |
| WO | 01/26581 A1 | 4/2001 |
| WO | WO 01/39670 A1 | 6/2001 |
| WO | 01/45589 A1 | 6/2001 |
| WO | 01/56499 A1 | 8/2001 |
| WO | WO 02/28312 A1 | 4/2002 |
| WO | WO 02/32284 A2 | 4/2002 |
| WO | WO 02/34124 A2 | 5/2002 |
| WO | WO 02/39890 A2 | 5/2002 |
| WO | WO 02/071953 A2 | 9/2002 |

OTHER PUBLICATIONS

Benderev, Theodore V., MD, Anchor Fixation and Other Modifications of Endoscopic Bladder Neck Suspension, Urology, Vol 40, No. 5, pp. 409–418 (Nov. 1992).

Das, Sakti et al., Laparoscopic Colpo–Suspension, The Journal of Urology, vol. 154, pp. 1119–1121 (Sep. 1995).

Gilja, Ivan et al., A Modified Raz Bladder Neck Suspension Operation (Transvaginal Burch), The Journal of Urology, vol. 153, pp. 1455–1457 (May 1995).

Gittes, Ruben F. et al., No–Incision Pubovaginal Suspension for Stress Incontinence, The Journal of Urology, vol. 138 (Sep. 1987).

Holschneider, C. H., et al., The Modified Pereyra Procedure in Recurrent Stress Urinary Incontinence: A 15–year Review, Obstetrics & Gynecology, vol. 83, No. 4, pp. 573–578 (Apr. 1994).

Horbach, Nicollette S., et al., Instruments and Methods, A Suburethral Sling Procedure with Polytetrafluoroethylene for the Treatment of Genuine Stress Incontinence in Patients with Low Urethral Closure Pressure, Obstetrics & Gynecology, vol. 71, No. 4, pp. 648–652 (Apr. 1998).

Klutke, Carl et al., The Anatomy of Stress Incontinence: Magnetic Resonance Imaging of the Female Bladder Neck and Urethra, The Journal of Urology, Vol 143, pp. 563–566 (Mar. 1990).

Klutke, John James et al., Transvaginal Bladder Neck Suspension to Cooper's Ligament: A Modified Pereyra Procedure, Obstetrics & Gynecology, vol. 88, No. 2, pp. 294–296 (Aug. 1996).

Kovac, S. Robert, et al, Pubic Bone Suburethral Stabilization Sling for Recurrent Urinary Incontinence, Obstetrics & Gynecology, vol. 89, No. 4, pp. 624–627 (Apr. 1997).

Kovac, S. Robert, et al, Pubic Bone Suburethral Stabilization Sling: A Long Term Cure for SUI?, Contemporary OB/GYN, 10 pages (Feb. 1998).

Kovac, S. Robert, Follow–up of the Pubic Bone Suburethral Stabilization Sling Operation for Recurrent Urinary Incontinence (Kovac Procedure), Journal of Pelvic Surgery, pp. 156–160 (May 1999).

Leach, Gary E., et al., Female Stress Urinary Incontinence Clinical Guidelines Panel Report on Surgical Management of Female Stress Urinary Incontinence, American Urological Association, vol. 158, pp. 875–880 (Sep. 1997).

Leach, Gary E., MD, Bone Fixation Technique for Transvaginal Needle Suspension, Urology Vol XXXI, No. 5, pp. 388–390 (May 1988).

Loughlin, Kevin R. et al., Review of an 8–Year Experience with Modifications of Endoscopic Suspension of the Bladder Neck for Female Stress Incontinence, The Journal of Urology, vol. 143, pp. 44–45 (1990).

McGuire, Edward J. et al., Experience with Pubovaginal Slings for Urinary Incontinence at the University of Michigan, Journal of Urology, vol. 138, pp. 90–93(1987).

McGuire, Edward J., M.D., The Sling Procedure for Urinary Stress Incontinence, Profiles in Urology, pp. 3–18.

McGuire, Edward J. et al., Abdominal Fascial Slings, Slings, Raz Female Urology, p. 369–375 (1996).

McKiel, Charles F. Jr., et al, Marhsall–Marchetti Procedure Modification, Vol 96, pp. 737–739 (Nov. 1966).

Mitek Brochure, Therapy of Urinary Stress Incontinence in Women Using Mitek GIII Anchors, By Valenzio C. Mascio, MD.

Morgan, J. E. et al., The Marlex Sling Operation for the Treatment of Recurrent Stress Urinary Incontinence: A 16–Year Review, American Obstetrics Gynecology, vol. 151, No. 2, pp. 224–226 (Jan. 1998).

Parra, R. O., et al, Experience with a Simplified technique for the Treatment of Female Stress Urinary Incontinence, British Journal of Urology, pp. 615–617 (1990).

Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advanced Surgical Techniques, vol. 9, No. 1 pp. 45–50 (1999).

Pereyra, Armand J. et al, Pubourethral Supports in Perspective: Modified Pereyra Procedure for Urinary Incontinence, Obstetrics and Gynecology, vol. 59, No. 5, pp 643–648 (May 1982).

Petros, Peter E. Papa et al., Part IV: Surgical Applications of the Theory–Development of the Intravaginal Sling Pklasty (IVS) Procedure, Scandinavian Journal of Neurourology and Urodynamics, Sup 153, pp. 53–54 (1993).

Petros, Peter E. Papa et al., The Role of a Lax Posterior Vaginal Fornix in the Causation of Stress and Urgency Symptoms: A Preliminary Report, Acta Obstet Gynecol Scand, Vol 69, Sup 153, pp. 71–73 (1990).

Raz, Shlomo, et al., The Raz Bladder Neck Suspension Results in 206 Patients, The Journal of Urology, pp. 845–846 (1992).

Raz, Shlomo, MD, Modified Bladder Neck Suspension for Female Stress Incontinence, Urology, vol. XVII, No. 1, pp. 82–85 (Jan. 1981).

TVT Tension–free Vaginal Tape, Gynecar, Ehticon, Inc., 23 pages (1999).

Waxman, Steve et al., Advanced Urologic Surgery for Urinary Incontinence, The Female Patient, pp. 93–100, Vol 21 (Mar. 1996).

Webster, George D., Female Urinary Incontinence, Urologic Surgery, pp. 665–679.

Winter, Chester C., Peripubic Urethropexy for Urinary Stress Incontinence in Women, Urology, vol. XX, No. 4, pp. 408–411 (Oct. 1982).

Zimmern, Phillippe E. et al., Four–Corner Bladder Neck Suspension, Vaginal Surgery for the Urologist, Vol 2, No. 1, pp. 29–36 (Apr. 1994).

Albert H. Aldridge, B.S., M.D., F.A.C.S., Transplantation of Fascia for Relief of Urinary Stress Incontinence, American Journal of Obstetrics and Gynecology,v. 44, pp. 398–411, (1948).

Victor Fray Marshall et al. The Correction of Stress Incontinence by Simple Vesicourethral Suspension, Surgery, Gynecology and Obstetrics, vol. A6188, pp. 509–518 (1949).

Henry Roberts, M.D., Cystourethrography in Women, Deptment of Obstetrics and Gynaecology, University of Liverpool, may 1952, vol. XXXV, No. 293, pp. 253–259.

T.N.A. Jeffcoate, The Results of the Aldridge Sling Operation for Stress Incontinence, Journal of Obstetrics and Gynaecology, pp. 36–39 (1956).

W.E. Studiford: Transplantation of Abdominal Fascia for the Relief of Urinary Stress Incontinence, American Journal of Obstetrics and Gynecology, pp. 764–775 (1944).

W.R. Sloan et al., Stress Incontinence of Urine: A Retrospective Study of the Complications and Late Results of Simple Suprapbuic Suburethral Fascial Slings, The Journal of Urology, vol. 110, pp. 533–536 (Nov. 1973).

G. Narik et.al., A Simplified Sling Operation Suitable for Routine Use, Gynecological and Obstetrical Clinic, University of Vienne, vol. 84, No 3, pp. 400–405, (Aug. 1, 1962).

Jerry Blaivas et al., Type III Urinary Incontinence: Importance of Proper Diagnosis and Treatment, Surgical Forum, pp. 473–475, (1984).

Jerry Blaivas, Commentary Pubovaginal Sling Procedure, Surgery for Female Urinary Incontinence, Current Operative Urology, pp. 93–100 (1990).

Edward J. McGuire et al., Experience With Pubovaginal Slings for Urinary Incontinence at the University of Michigan, Journal og Urology, vol. 138, pp. 525–526 (1987).

J. Chassar Moir et.al., The Gauze–Hammock Operation, The Journal of Obstetrics and Gynaecology of British Commonwealth, vol. 75 No. 1, pp. 1–9 (Jan. 1968).

C. Paul Hodgkinson et.al., Urinary Stress Incontinence in the Female, Department of Gynecology and Obstetrics, henry Ford Hospital, Vol 10, No. 5, pp. 493–499, (Nov. 1957).

Armand J. Pereyra, M.D., F.A.C.S., A Simplified Surgical Procedure for Correction of Stress Incontinence in Women, West.J.Surg., Obst. & Gynec, p. 223–226, (Jul.–Aug. 1959).

Robert Zacharin, The Suspensory Mechanism of the Female Urethra, Journal of Anatomy, vol. 97, Part 3, pp. 423–427 (1963).

M. Asmussen et.al., Simultaneous Urethro–Cystometry With a New Technique, Scand J Urol Nephrol 10, p. 7–11 (1976).

Edward J. McGuire et al., Pubovaginal Sling Procedure for Stress Incontinence, The Journal of Urology, vol. 119, pp. 82–84 (Jan. 1978).

Jerry Blaivas et al., Pubovaginal Fascial Sling for the Treatment of Complicated Stress Urinary Incontinence, The Journal of Urology, vol. 145, pp. 1214–1218 (Jun. 1991).

Edward J. McGuire, M.D., Abdominal Procedures for Stress Incontinence, Urologic Clinics of North America, pp. 285–290, vol. 12, No. 2 (May 1985).

Jeffrey R. Woodside et al., Suprapubic Endoscopic Vesical Neck Suspension for the Management of Urinary Incontinence in Myelodysplastic Girls, The Journal of Urology, vol. 135, pp. 97–99 (Jan. 1986).

David A. Richardson et al., Delayed Reaction to the Dacron Buttress Used in Urethropexy, The Journal of Reproductive Medicine, pp. 689–692, vol. 29, No. 9 (Sep. 1984).

L. Henriksson et al., A Urodynamic Evaluation of the Effects of Abdominal Urethrocystopexy and Vaginal Sling Urethroplasty in Women with Stress Incontinence, Am. J. obstet. Gynecol. Vol 131, No 1, pp. 77–82 (Mar 1, 1978).

Robert Zacharin et al., Pulsion Enterocele: Long–Term Results of an Abdominoperineal Technique, Obstetrics & Gynecology, vol. 55 No. 2, pp. 141–148 (Feb. 1980).

Thomas A. Stamey, M.D., Endoscopic Suspension of the Vesical Neck for Urinary Incotinence in Females, Ann. Surg., vol. 192 No. 4, pp. 465–471 (Oct. 1980).

Ulf Ulmsten et al., The Unstable Female Urethra, Am. J. Obstet. Gynecol., vol. 144 No. 1, pp. 93–97 (Sep. 1, 1982).

A. Ingelman–Sunberg et al., Surgical Treatment of Female Urinary Stress Incontinence, Contr. Gynec. Obstet., vol. 10, pp. 51–69 (1983).

Ulf Ulmsten et al., Different Biochemical Composition of Connective Tissue in Continent, Acta Obstet Gynecol Scand, pp. 455–457 (1987).

Bjarne C. Eriksen et al., Long–Term Effectiveness of the Burch Colposuspension in Female Urinary Stress Incontinence, Acta Obstet Gynecol Scand, 69, pp. 45–50 (1990).

H. Enzelsberger et al., Urodynamic and Radiologic Parameters Before and After Loop Surgery for Recurrent Urinary Stress Incontinence, Acta Obstet Gynecol Scand, 69, pp. 51–54 (1990).

Peter E. Papa Petros et al., An Integral Theory of Female Urinary Incontinence, Acta obstetricia et Gynecologica Scandinavica, vol. 69 Sup. 153, pp. 7–31 (1990).

Peter E. Papa Petros et al., Pinch Test for Diagnosis of Stress Urinary Incontinence, Acta Obstet Gynecol Scand, Vol 69, Sup 153, pp. 33–35 (1990).

Peter E. Papa Petros et al., Cough Transmission Ratio: An Indicator of Suburethral Vaginal Wall Tension Rather Than Urethral Closure?, Acta Obstet Gynecol Scand, Vol 69, Sup 153, pp. 37–39 (1990).

Peter E. Papa Petros et al., The Tuck Procedure: A Simplified Vaginal Repair for Treatment of Female Urinary Incontinence, Acta Obstet Gynecol Scand, Vol 69, Sep 153, pp. 41–42 (1990).

Peter E. Papa Petros et al., The Autogenic Ligament Procedure: A Technique for Planned Formation of an Artificial Neo–Ligament, Acta Obstet Gynecol Scand, Vol 69, Sup 153, pp. 43–51 (1990).

Peter E. Papa Petros et al., The Combined Intravaginal Sling and Tuck Operation an Ambulatory Procedure for Cure of Stress and Urge Incontinence, Acta Obstet Gynecol Scand, Vol 69, Sup 153, pp. 53–59 (1990).

Peter E. Papa Petros et al., Cure of Urge Incontinence by the Combined Intravaginal Sling and Tuck Operation, Acta Obstet Gynecol Scand, Vol 69, Sup 153, pp. 61–62 (1990).

Peter E. Papa Petros et al., The Tethered Vagina Syndrome, Post Surgical Incontinence and I–Plasty Operation for Cure, Acta Obstet Gynecol Scand, Vol 69, Sup 153, pp. 63–67 (1990).

Peter E. Papa Petros et al., Non Stress Non Urge Female Urinary Incontinence—Diagnosis and Cure: A Preliminary report, Acta Obstet Gynecol Scand, Vol 69, Sup 153, pp. 69–70 (1990).

Peter E. Papa Petros et al., The Role of a Lax Posterior Vaginal Fornix in the Causation of Stress and Urgency Symptoms: A Preliminary Report, Acta Obstet Gynecol Scand, Vol 69, Sup 153, pp. 71–73 (1990).

Peter E. Papa Petros et al., Pregnancy Effects on the Intravaginal Sling Operation, Acta Obstet Gynecol Scand, Vol 69, Sup 153, pp. 77–79 (1990).

Peter E. Papa Petros et al., An Analysis of Rapid Pad Testing and the History for the Diagnosis of Stress Incontinence, Acta Obstet Gynecol Scand, Vol 71, pp. 529–536 (1992).

Peter E. Papa Petros et al., Bladder Instability in Women: A Premature Activation of the Micturition Reflex, Scandinavian Journal of Neurourology and Urodynamics, Sup 153, pp. 235–239 (1993).

Peter E. Papa Petros et al., Part I: Theoretical, Morphological, Radiographical Correlations and Clinical Perspective, Scandinavian Journal of Neurourology and Urodynamics, Sup 153, pp. 5–28 (1993).

Peter E. Papa Petros et al., Part II: The Biomechanics of Vaginal Tissue and Supporting Ligaments with Special Relevance to the Pathogenesis of Female Urinary Incontinence, Scandinavian Journal of Neurourology and Urodynamics, Sep 153, pp. 29–40 (1993).

Peter E. Papa Petros et al., Part III: Surgical Principles Deriving From the Theory, Scandinavian Journal of Neurourology and Urodynamics, Sup 153, pp. 41–52 (1993).

Peter E. Papa Petros et al., Part IV: Surgical Applications of the Theory—Development of the Intravaginal Sling Plasty (IVS) Procedure, Scandinavian Journal of Neurourology and Urodynamics, Sup 153, pp. 53–54 (1993).

Peter E. Papa Petros et al., An Anatomical Basis for Success and Failure of Female Incontinence Surgery, Scandinavian Journal of Neurourology and Urodynamics, Sup 153, pp. 55–60 (1993).

Peter E. Papa Petros et al., The Development of the Intravaginal Slingplasty Procedure: IVS II—(With Bilateral "Tucks"), Scandinavian Journal of Neurourology and Urodynamics, Sup 153, pp. 61–67 (1993).

Peter E. Papa Petros et al., Further Development of the Intravaginal Slingplasty Procedure—IVS III—(With Midline "Tuck"), Scandinavian Journal of Neurourology and Urodynamics, Sup 153, p. 69–71 (1993).

Peter E. Papa Petros et al., The Further Development of the Intravaginal Slingplasty Procedure—IVS IV—(With "Double Breasted" Unattached Vaginal Flap Repair and "Free" Vaginal Tapes), Scandinavian Journal of Neurourology and Urodynamics, Sup 153, p. 73–75 (1993).

Peter E. Papa Petros et al., The Further Development of the Intravaginal Slingplasty Procedure—IVS V—(With "Double Breasted" Unattached Vaginal Flap Repair and Permanent Sling)., Scandinavian Journal of Neurourology and Urodynamics, Sup 153, pp. 77–79 (1993).

Peter E. Papa Petros et al., The Intravaginal Slingplasty Procedure: IVS VI—Further Development of the "Double Breasted" Vaginal Flap Repair—Attached Flap, Scandinavian Journal of Neurourology and Urodynamics, Sup 153, pp. 81–84 (1993).

Peter E. Papa Petros et al., The Free Graft Procedure for Cure of the Tethered Vagina Syndrome, Scandinavian Journal of Neurourology and Urodynamics, Sup 153, pp. 85–87(1993).

Peter E. Papa Petros et al., The Posterior Fornix Syndrome: A Multiple Symptom Complex of Pelvic Pain and Abnormal urinary Symptoms Deriving From Laxity in the Posterior Fornix of Vagina, Scandinavian Journal of Neurourology and Urodynamics, Sup 153, p. 89–93 (1993).

John DeLancey, MD, Structural Support of the Urethra as it relates to Stress Urinary Incontinence: The Hammock Hypothesis, Am J Obstet Gynecol, Vol 170 No 6, pp. 1713–1723 (Jun. 1994).

Ulf Ulmsten et al., Intravaginal Slingplasty (IVS): An Ambulatory Surgical Procedure for Treatment of Female Urinary Incontinence, Scand J Urol Nephrol, Vol 29, pp. 75–82 (1995).

Arieh Bergman et al., Three Surgical Procedures for Genuine Stress Incontinence: Five–Year Follow–Up of a Prospective Randomized Study, Am J Obstet Gynecol, Vol 173 No 1, pp. 66–71 (Jul. 1995).

Peter E. Papa Petros et al., Urethral Pressure Increase on Effort Originates From Within the Urethra, and Continence From Musculovaginal Closure, Scandinavian Journal of Neurourology and Urodynamics, pp. 337–350 (1995).

U. Ulmsten, Female Urinary Incontinence—A Symptom, Not a Urodynamic Disease. Some Theoretical and Practical Aspects on the Diagnosis a Treatment of Female Urinary Incontinence, International Urogynecology Journal, Vol 6, pp. 2–3 (1995).

U. Ulmsten et al., An Ambulatory Surgical Procedure Under Local Anesthesia for Treatment of Female Urinary Incontinence, International Urolgynecology Journal, Vol 7, pp. 81–86, (1996).

Peter E. Papa Petros, Development of Generic Models for Ambulatory Vaginal Surgery—Preliminary Report,International Urogynecology Journal, pp. 20–27 (1998).

U. Ulmsten et al., A Multicenter Study of Tension–Free Vaginal Tape (TVT) for Surgical Treatment of Stress Urinary Incontinence, International Urogynecology Journal, Vol 9, pp. 210–213 (1998).

Peter E. Papa Petros et al., Medium–Term Follow–Up of the Intravaginal Slingplasty Operation Indicates Minimal Deterioration of Urinary Continence With Time, (3 pages) (1999).

Ulf Ulmsten et al., A Three Year Follow Up of Tension Free Vaginal Tape for Surgical Treatment of Female Stress Urinary Incontinence, British Journal of Obstetrics and Gynaecology, Vol 106, pp. 345–350 (1999).

Raymond Rackley, MD., Synthetic Slings: Five Steps for Successful Placement, Urology Times, p. 46,48,49 (Jun. 2000).

Peter E. Papa Petros, New Ambulatory Surgical Methods Using an Anatomical Classification of Urinary Dysfunction Improve Stress, Urge and Abnormal Emptying, Int. Urogynecology Journal Pelvic Floor Dystfunction, vol. 8 (5), pp. 270–277, (1997).

Stuart Stanton,Springer–Veglag, Surgery of Female Incontinence, pp. 105–113 (1986).

Raymond R. Rackley, M.D. et al. Tension–free Vaginal Tape and Percutaneous Vaginal Tape Sling Procedures, Techniques In Urology (2001), vol. 7, No. 2, pp. 90–100.

John Klutke, M.D. et al, The promise of tension–free vaginal tape for female SUI, Contemporary Urology, 7 pages (Oct. 2000).

TVT Tension–free Vaginal Tape, Gynecare, Ethicon, Inc., 23 pages (1999).

Vesica® Percutaneous Bladder Neck Stabilization Kit, A New Approach to Bladder Neck Suspension, Microvasive® Boston Scientific Corporation, 4 pages (1995).

Vesica® Sling Kits, Simplifying Sling Procedures, Microvasive® Boston Scientific Corporation, 4 pages (1998).

Peter E. Papa Petros et al., Cure of Stress Incontinence by Repair of External Anal Sphincter, Acat Obstet Gynecol Scand, Vol 69, Sup 153, p. 75 (1990).

Peter Petros et al., Anchoring the Midurethra Restores Bladder–Neck Anatomy and Continence, The Lancet, Vol 354, pp. 997–998 (Sep. 18, 1999).

Ross Decter, Use of the Fascial Sling for Neurogenic Incontinence Lessons Learned, The Journal of Urology, vol. 150 pp. 683–686 (Aug. 1993).

Julia Spencer et al., A Comparison of Endoscopic Suspension of the Vesical Neck with Suprapubic Vesicourethropexy for Treatment of Stress Urinary Incontinence, The Journal of Urology, vol. 137, pp. 411–415 (Mar. 1987).

Tohru Araki et al., The Loop–Loosening Procedure for Urination Difficulties After Stamey Suspension of the Vesical Neck, The Journal of Urology, vol. 144, pp. 319–323 (Aug. 1990).

George Webster et al., Voiding Dysfunction Following Cystourethropexy: Its Evaluation and Management, The journal of Urology, vol. 144, pp. 670–673 (Sep. 1990).

Donald R. Ostergard et al., Urogynecology and Urodynamics Theory and Practice, pp. 569–579 (1996).

John C. Burch, Urethrovaginal Fixation to Cooper's Ligament for Correction of Stress Incontinence, Cystocele, and Prolapse, Am. J. Obst. & Gyn, vol. 31, pp. 281–290 (1961).

G. A. McIndoe et al., The Aldridge Sling Procedure in the Treatment of Urinary Stress Incontinence, Aust. N Z Journal of Obstet Gynecology, pp. 238–240 (Aug. 1987).

J. Kersey, The Gauze Hammock Sling Operation in the Treatment of Stress Incontience, British Journal of Obstetrics Gynecology, pp 945–949 (Oct. 1983).

John H. Ridley, Appraisal of the Goebell–Frangenheim–Stoeckel Sling Procedure, Am. J. Obst. & Gyn., vol. 95, pp. 714–721 (Jul. 1966).

J. E. Morgan, A Sling Operation, Using Marlex Polypropylene Mesh, for the Treatment of Recurrent Stress Incontinence, Am. J. Obst. & Gynecol, pp. 369–377 (Feb. 1970).

Stuart Stanton, Suprapubic Approaches for Stress Incontinence in Women, Journal of American Geriatic Society, vol. 38, pp. 348 (1990).

G. Narik, et al., A Simplified Sling Operation Suitable for Routine Use, Am. J. Obst. & Gyn., vol. 84, pp. 400–440 (1962).

Mickey Karram et al., Patch Procedure: Modified Transvaginal Fascia Lata Sling for Recurrent for Severe Stress Urinary Incontinence, vol. 75, pp. 461–463 (Mar. 1990).

Pat O'Connell, Combined Raz Urethral Suspension and McGuire Pubovaginal Sling for Treatment of Complicated Stress Urinary Incontinence, Journal of Arkansas Medical Society, vol. 88, pp. 389–392 (Jan. 1992).

Fred E. Bryans, Marlex Gauze Hammock Sling Operation with Cooper's Ligament Attachment in the Management of Recurrent Urinary Stress Incontinence, American Journal of Obstetrics and Gynecology, vol. 133, pp. 292–294 (Feb. 1979).

A. Korda et al., Experience with Silastic Slings for Female Urinary Incontience, Aust NZ J. Obstet Gynaecol, vol. 29, pp. 150–154 (May 1989).

David H. Nichols, The Mersilene Mesh Gauze–Hammock for Severe Urinary Stress Incontinence, Obstetrics and Gynecology, vol. 41, pp. 88–93 (Jan. 1973).

Jeffrey P. Norris, et al., Use of Synthetic Material in Sling Surgery: A Minimally Invasive Approach, Journal of Endourology, vol. 10, pp. 227–230 (Jun. 1996).

Jong M. Choe et al., Gore–Tex Patch Sling: 7 Years Laters, Urology, vol. 54, pp. 641–646 (1999).

David R. Staskin et al., The Gore–Tex Sling Procedure for Female Sphincteric Incontinence: Indications, Technique, and Results, World Journal of Urology, vol. 15, pp. 295–299 (1997).

C. Falconer, et al., Influence of Different Sling Materials of Connective Tissue Metabolism in Stress Urinary Incontinent Women, International Urogynecology Journal, Supp. 2, pp. S19–S23 (2001).

Mark D. Walters, Percutaneous Suburethral Slings: State of the Art, Presented at the conference of the American Urogynecologic Society, Chicago, (Oct. 2001).

Cook/Ob Gyn®, Urogynecology, Copyright Cook Urological Inc., pp. 1–36 (1996).

Shlomo Raz, Female Urology, pp. 80–86, 369–398, 435–442 (1996).

SLING ASSEMBLY WITH SECURE AND CONVENIENT ATTACHMENT

CROSS REFERENCE TO RELATED APPLICATIONS

The present application is a continuation-in-part of U.S. patent application Ser. No. 10/005,837, filed Nov. 9, 2001 pending and U.S. patent application Ser. No. 09/917,443 filed Jul. 27, 2001 pending and U.S. Patent Application No. 09/917,562 filed Jul. 27, 2001 pending and claims priority thereto and of U.S. Provisional Application Ser. No. 60/269,829, filed Feb. 20, 2001, and U.S. Provisional Application Ser. No. 60/281,350, filed Apr. 4, 2001; and U.S. Provisional Application Ser. No. 60/295,068, filed Jun. 1, 2001, and U.S. Provisional Application No. 60/306,915, filed Jul. 20, 2001, and U.S. Provisional Patent Application No. 60/332,330, filed Nov. 20, 2001, entitled, "Sling Assembly Articles" (all of whose contents are fully incorporated herein by reference).

BACKGROUND

Urinary incontinence is a significant health concern worldwide. Incontinence may occur when the pelvic floor weakens. There are five basic types of incontinence: stress incontinence, urge incontinence, mixed incontinence, overflow incontinence and functional incontinence. There are a large number of surgical interventions and procedures for addressing incontinence.

Some surgeons are slow to adopt promising new surgical techniques for treating incontinence for a variety of reasons. Some are simply unwilling to try new instrumentation that seems unfamiliar. Others may find new instrumentation inconvenient or awkward.

A variety of surgical procedure options are currently available to treat incontinence. Depending on age, medical condition, and personal preference, surgical procedures can be used to completely restore continence. One type of procedure, found to be an especially successful treatment option for SUI in both men and women, is a sling procedure.

A sling procedure is a surgical method involving the placement of a sling to stabilize or support the bladder neck or urethra. There are a variety of different sling procedures. Descriptions of different sling procedures are disclosed in U.S. Pat. Nos. 5,112,344; 5,611,515; 5,842,478; 5,860,425; 5,899,909; 6,039,686, 6,042,534 and 6,110,101.

Sling procedures differ in the type of material used for the sling, the method of anchoring the sling material in the body and how the sling material is inserted in the body. The time required for a surgical procedure varies, but is preferably as short as possible. This factor is frequently reported in urology and gynecology literature. See Atherton M. J., et al., *A Comparison of Bladder Neck Movement and Elevation After Tension-free Vaginal Tape and Colposuspension*, British Journal of Obstetrics and Gynaecology, Nov. 2000, Vol. 17, p. 1366–1370, Nilsson et al, *The Tension-free Vaginal Tape Procedure is Successful in the Majority of Women with Indications for Surgical Treatment of Urinary Stress Incontinence*, British Journal of Obstetrics and Gynaecology, April 2001, Vol. 108, P. 414–419; and Ulmsten et al., *An Ambulatory Surgical Procedure Under Local Anesthesia For Treatment of Female Urinary Incontinence*, Int. Urogynecol. J. (1996), v. 7, pps. 81–86.

Although serious complications associated with sling procedures are infrequent, they do occur. Complications include urethral obstruction, development of de novo urge incontinence, hemorrhage, prolonged urinary retention, infection, and damage to surrounding tissue and sling erosion.

The Tension-free Vaginal Tape (TVT) procedure (available from Ethicon, of N.J.) utilizes a Prolene™ nonabsorbable, polypropylene mesh. The mesh is a substantially flat, rectangular knitted article. The mesh includes a plurality of holes that are sized to allow tissue ingrowth to help avoid infection. A plastic sheath surrounds the mesh and is used to insert the mesh. During the sling procedure, incisions are made in the abdominal (i.e. suprapubic) area and in the vaginal wall. Two curved, relatively large (5 mm or larger) needle-like elements are each connected to an end of the vaginal sling mesh. A sling-free, sharp tip end of one of the needle-like elements is initially pushed through the vaginal incision and into the paraurethral space. Using a handle attached to the needle, the needle is angulated laterally (for example, to the right) to perforate the endopelvic fascia, pushed through the retropubic space and passed through the abdominal incision. The handle is disconnected and the needle is then withdrawn through the abdominal wall, thereby threading a portion of the sling through the tissue of the patient. The handle is then connected to the other needle and the technique is repeated on the contralateral side, so that the mesh is looped beneath the bladder neck or urethra. The sling is positioned to provide appropriate support to the bladder neck or urethra. At the end of the procedure, the sling ends are cut at the abdominal wall, the sheath is removed and all incisions are closed.

Complications associated with the TVT procedure and other known sling procedures include injury to blood vessels of the pelvic sidewall and abdominal wall, hematomas, urinary retention, and bladder and bowel injury due to passage of large needles. One serious disadvantage of the TVT procedure, particularly for surgeons unfamiliar with the surgical method, is the lack of information concerning the precise location of the needle tip relative to adjacent pelvic anatomy. A cadaver study has indicated that the TVT needle is placed in close proximity to sensitive tissue such as superficial epigastric vessels, inferior epigastric vessels, the external iliac vessel and the obturator. See, Walters, Mark D., *Percutaneous Suburethral Slings: State of the Art*, presented at the conference of the American Urogynecologic Society, Chicago (October 2001).

If the TVT needle tip is allowed to accidentally pass across the surface of any blood vessel, lymphatic duct, nerve, nerve bundle or organ, serious complications can arise. These shortcomings, attempts to address these shortcomings and other problems associated with the TVT procedure are disclosed in PCT publication nos. PCT WO 00/74633, PCT WO 00/74613 and PCT WO 00/74594.

Additional problems are associated with the TVT procedure. Removal and reuse of the handle of the TVT product is a cumbersome, time consuming process, requiring the surgeon to manually rotate the handle until the handle is unscrewed from the needle. Reusing the handle presents a contamination risk, particularly if the handle and screw threads are not properly cleaned and sterilized after use on the patient.

BRIEF SUMMARY

The present invention includes surgical instruments, articles and procedures for urological applications, particularly incontinence surgical procedures.

In one aspect, the present invention comprises a surgical assembly for treating incontinence. The assembly comprises an elongate needle, a sling and a coupler. The needle is sized and shaped to be initially inserted through an abdominal incision and to then emerge from a vaginal incision. The needle has an insertion end and an end opposite the insertion end. The insertion end of the needle is preferably blunt. The sling is constructed of a material that is capable of being implanted during the incontinence procedure.

The coupler has an elongate body with an axis. The body has a first end and a second end with surfaces for conveniently and securely connecting the coupler to the insertion end of the needle by moving the coupler and insertion end of the needle together in a substantially axial fashion.

The coupler is convenient and easy to connect to the needle. Preferably, the assembly has an Insertion Force (described in greater detail below) of no more than about fifteen pounds. More preferably, the Insertion Force is no more than about ten pounds. Even more preferably, the assembly has an Insertion Force of no more than about eight pounds.

Once the coupler and needle are connected, they should not separate, especially within the body. Preferably, after the needle is connected to the coupler, the assembly has a Separation Force (described in greater detail below) of at least about fifteen pounds, more preferably of at least about thirty pounds.

In another aspect, the present invention comprises the coupler described above. The first end of the coupler connects to a first needle. The second end of the coupler can be associated with a sling, insertion sheath or both.

Optionally, the coupler can comprise a needle adapter for connecting a first needle to a second needle. In this embodiment, the second end of the coupler receives an end of a second needle so that the coupler and first needle may guide the second needle through the body.

In another aspect, the present invention comprises an improved method of treating incontinence in a female patient. The method comprises the steps of: i) providing a surgical mesh, and a removable synthetic insertion sheath, ii) providing a needle that is sized and shaped to be initially inserted through a suprapubic incision and to then emerge from a vaginal incision, iii) providing a coupler having an axis, the coupler having a first end and a second end with surfaces for conveniently and securely connecting the coupler to an insertion end of the needle, iv) creating at least one vaginal incision, v) creating at least one suprapubic incision, vi) passing the leading end of the needle initially through the suprapubic incision and then through the vaginal incision, vii) then connecting the coupler to the needle by moving the coupler and insertion end of the needle together while the insertion end of the needle protrudes from the vaginal incision, viii) implanting the sling by moving the leading end of the needle from the vaginal incision toward the suprapubic incision, and ix) then removing the synthetic insertion sheath.

Preferably, the step of connecting the coupler to the needle by moving the coupler and insertion end of the needle together includes the step of: pushing the coupler onto the insertion end of the needle in a substantially axial fashion.

In another aspect, the present invention comprises an improved surgical method including the steps of i) providing a first needle that is sized and shaped to be initially inserted through an abdominal incision and to then emerge from a vaginal incision, the needle having an insertion end and an end opposite the insertion end, ii) providing a coupler having an axis, the coupler having a first end and a second end with surfaces for conveniently and securely connecting the coupler to the insertion end of the needle, iii) providing a second needle that is sized and shaped to be initially inserted through a vaginal incision and to then emerge from an abdominal incision; the second needle being attached to a synthetic surgical mesh, and a removable synthetic insertion sheath, iv) creating at least one vaginal incision, v) creating at least one abdominal incision, vi) initially passing the first needle through the abdominal incision and then through the vaginal incision, vii) connecting the second end of the coupler to the insertion end of the first needle, viii) connecting the first end of the coupler to the second needle; and ix) guiding the second needle from the vaginal incision to the abdominal incision with the first needle to implant the sling.

BRIEF DESCRIPTION OF THE DRAWINGS

Other features and advantages of the present invention will be seen as the following description of particular embodiments progresses in conjunction with the drawings, in which:

FIGS. 11 and 12 are side schematic views wherein:

FIG. 11 shows a needle being inserted into a coupler according to an Insertion Force Test; and FIG. 12 shows a needle attached to the coupler and a Separation Force Test according to the present invention;

FIGS. 13 through 17 are perspective views sequentially showing the insertion of a needle suprapubically in accordance with one aspect of the present invention, wherein:

FIG. 13 shows the needle just passing an abdominal incision;

FIG. 14 illustrates the needle as the surgeon seeks to identify the tactile feel of the resistance provided in part by the posterior portion of the pubic bone;

FIG. 15 shows the needle as it passes along the posterior surface of the pubic bone which may be used as an anatomical guide for a surgeon as the needle approaches a vaginal incision;

FIG. 16 illustrates the needle as it passes out of a vaginal incision;

FIG. 17 is a perspective view of a sling attached to two needles according to an embodiment of the present invention;

DETAILED DESCRIPTION

The following description is meant to be illustrative only and not limiting. Other embodiments of this invention will be apparent to those of ordinary skill in the art in view of this description.

The present invention is directed to surgical instruments, and implantable articles for treating medical disorders such as incontinence or stress urinary incontinence (SUI) in both men and women. The present invention is also directed to improved surgical procedures that utilize the surgical articles. Although the invention as disclosed herein generally refers to SUI, treatment of other urological disorders, such as urge incontinence, fecal incontinence, mixed incontinence, overflow incontinence, functional incontinence, prolapse (e.g. vaginal and uterine), enteroceles (e.g. of the uterus or small bowel), rectoceles, cystoceles and other disorders are also included within the scope of the present invention. It is contemplated that the present invention may also be utilized in conjunction with concomitant procedures, such as, but not limited to, procedures for addressing cystocele, rectocele, vaginal prolapse and anatomic corrections.

Figure 1:
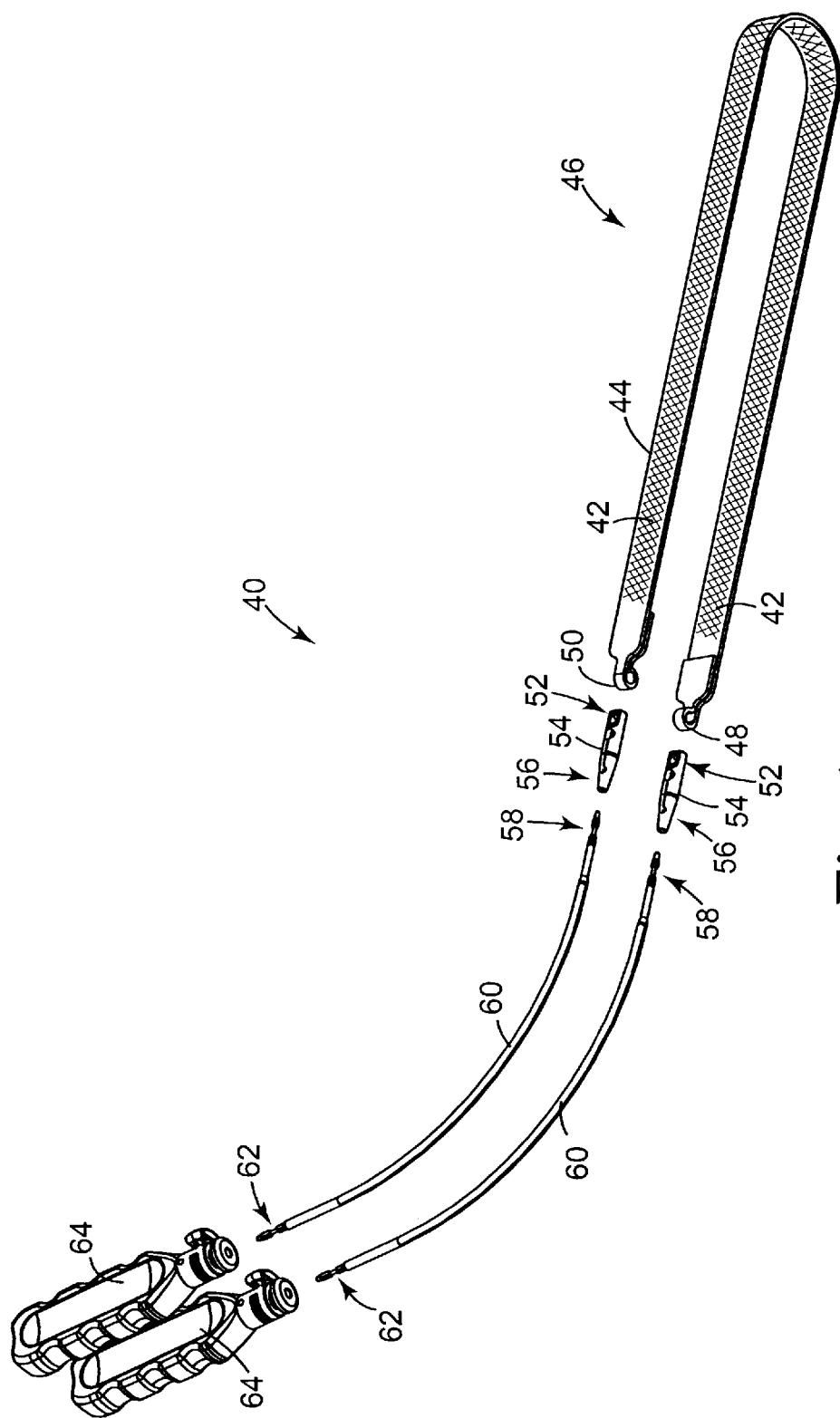
FIG. 1 is a perspective view of one embodiment of assembly according to the present invention.

In one aspect, the present invention comprises an assembly 40 for use in surgery. FIG. 1 illustrates a sling 42, a needle 60 and a dilator or coupler 54.

The needle 60 is preferably sized and shaped to pass initially through an abdominal incision and then emerge through a vaginal incision. Typically, the needle will have an elongate body and a pair of ends 58 and 62.

Figure 9:
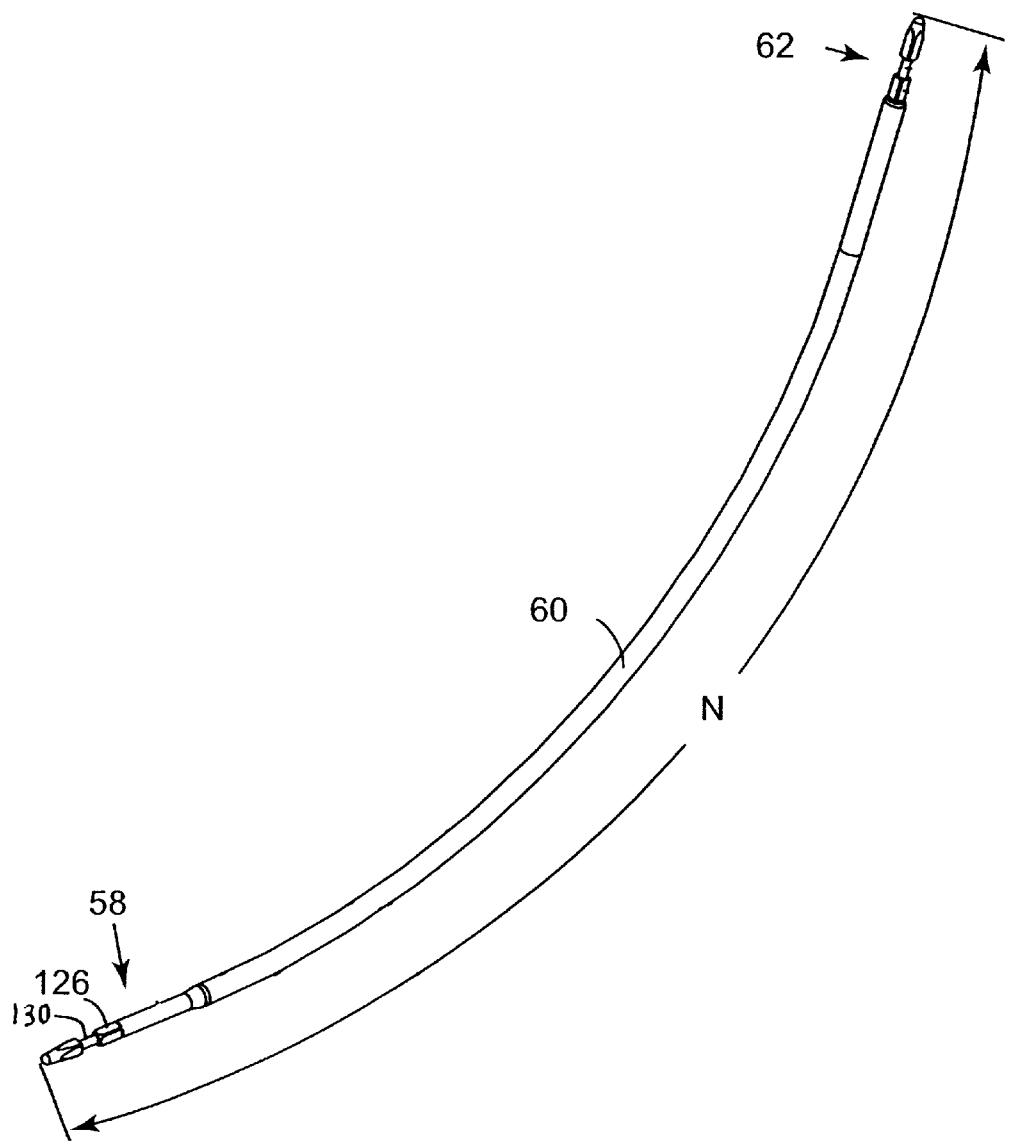
FIG. 9 is a perspective view of a needle according to the present invention.

FIG. 9 illustrates a curved needle 60. The needle 60 is preferably arc-shaped and includes end 58 and end 62. The ends or tip of the needle 60 are preferably not sharp, but may be tapered to afford easy passage through tissue while providing a blunt surface that avoids cutting sensitive tissue such as the bladder or urethra. In a preferred embodiment, the length of the needle 60 is approximately within the range of 16.5 cm to 24.1 cm (6.5 inches to 9.5 inches) and has a preferred external diameter of approximately 3.175 mm (0.125 inch). Preferably, the diameter of the needle 60 is small to reduce tissue trauma and increase control.

The needle 60 is preferably made of a malleable, yet durable, biocompatible surgical instrument material such as, but not limited to, stainless steel (e.g. 316 stainless steel or 17-4 stainless steel), titanium, Nitinol, polymers, plastics and other materials, including combinations of materials. The needle 60 should have sufficient structural integrity to withstand the various forces (e.g. forces caused by coupler attachment, and penetration/passage of the needle 60 through the various tissues) without undergoing any significant structural deformation. Optionally, the needles 60 could be sufficiently malleable to allow a practitioner or user of the device to modify the needle 60 to a desired shape and, thereby, optimize the procedural approach.

Figure 21:
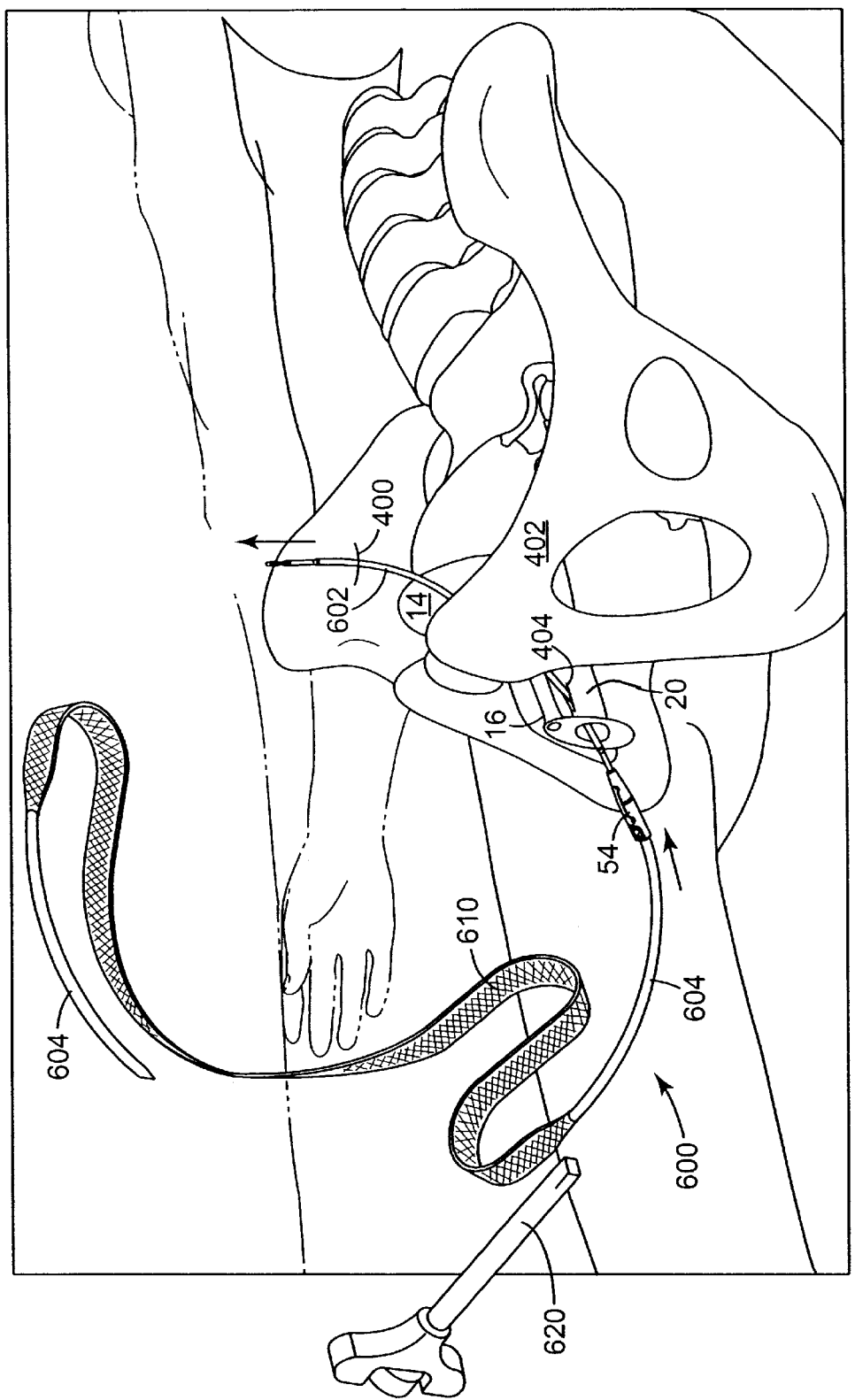
FIG. 21 is a perspective view of a first needle after it has been inserted suprapubically and emerges from a vaginal incision, a coupler connected to the first needle after the needle has been inserted suprapubically, and a second needle for implanting a sling that is associated with the other end of the coupler in preparation for being moved through the patient.

In another aspect of the present invention, different types of needles may be provided that need not serve the same purpose in a surgical procedure. FIG. 21 illustrates a suprapubic needle 602 (e.g. with a preferred diameter of about 4 mm, or less, more preferably about 3 mm) and a relatively larger sling associated needle 604 (e.g. with a diameter of 5 mm). Preferably, the sling associated needle has a sling assembly 610 (e.g. a sling mesh and insertion sheath) attached thereto.

The suprapubic needle 602 serves a different purpose than the sling associated needle 604. The suprapubic needle 602 is preferably small and has a blunt tip. The blunt tip is initially inserted through an abdominal or suprapubic incision 400 and then through a vaginal incision 404. Inserting a small, blunt needle in this fashion provides the surgeon with addition control in maneuvering through the anatomy of a patent and in avoiding sensitive tissue.

A surgical assembly according to an aspect of the present invention may include a coupler 54 adapted to be snapped onto the end of needle 602. The sling associated needle 604 may optionally include a sharp tip. The coupler receives the tip or end of the needle 604. Pushing upward on the sling associated needle 604 (e.g. with one hand) while optionally steering or guiding the tip of the needle 604 by holding needle 602 (e.g. with the other hand) is believed to provide better control over insertion of a prior art large needle that is initially inserted through the vaginal incision 404 and then through the suprapubic incision.

Alternatively, the coupler and/or needle 604can include surfaces for firm engagement and attachment between coupler and needle 604. Those surfaces can include mechanical interlocking structures, grasping structures or interference structures. Optionally, a biocompatible adhesive may be used to adhere the tip of sling associated needle 604 to the coupler/adapter.

Referring again to FIG. 1, the assembly includes a sling material 42 (e.g. as part of the sling assembly 46). As used herein, the terms "sling" or "article" or "mesh" or the phrases "implantable material" or "implantable article" or "sling mesh" (or combinations thereof) are used generally to describe a variety of materials including synthetic and non-synthetic materials. Typically, the implantable article will be elongate and substantially flat. It can be used as a hammock, sling, strip or support member. Optionally, the sling 42 can include a sling tensioning member 66 (e.g. as disclosed in U.S. patent appl. Ser. No. 09/917,562, filed Jul. 27, 2001).

While the sling 42 is preferably rectangular for treating SUI in females, other shapes are also contemplated. Depending on the treatment addressed (e.g. to provide hammock support for the bladder or bladder neck, or to address a rectocele, enterocele or prolapse) the slings may be any of a wide variety of shapes. As an example, the sling may be of the general shape of the slings described and shown in Moir et al., *The Gauze-Hammock Operation,* Journal of Obstetrics and Gynaecology of the British Commonwealth, Volume 75, No. 1, Pps. 1–9 (1968).

Suitable non-synthetic materials include allografts, homografts, heterografts, autologous tissues, cadaveric fascia and fascia lata.

Suitably synthetic materials for a sling include polymerics, and plastics and any combination of such materials may also be used in a kit of the present invention. Commercial examples of such materials include Marlex™, Prolene™, and Vaskutek™. Other examples of suitable materials include those disclosed in U.S. patent application Ser. No. 09/939,098 filed Aug. 24, 2001 (the entire contents of which are herein incorporated by reference). Specific examples of synthetic sling materials include, but are not limited to polypropylene, polyethylene, nylon, PLLA and PGA.

The sling material may be resorbable, absorbable or non-absorbable. Optionally portions may be absorbable and other portions may be non-absorbable.

In one aspect of the invention, the sling 42 may comprise a mesh material. The mesh material comprises one or more woven, knitted or inter-linked filaments or fibers that form multiple fiber junctions throughout the mesh. The fiber junctions may be formed via weaving, knitting, braiding, bonding, ultrasonic welding or other junction forming techniques, including combinations thereof. In addition, the size of the resultant openings or pores of the mesh may be sufficient to allow tissue in-growth and fixation within surrounding tissue. As an example, not intended to be limiting, the holes may comprise polygonal shaped holes with diagonals of 0.132 inches and 0.076 inches. Holes much smaller than this are not preferred as they may facilitate bacterial colonization.

The quantity and type of fiber junctions, fiber weave, pattern, and material type influence various sling properties or characteristics. Non-mesh sling configurations are also included within the scope of the invention. As another example, not intended to be limiting, the mesh may be woven polypropylene monofilament, knitted with a warp tricot. The stitch count may be 27.5 courses/inch (+ or −2 courses ) and 13 wales/inch (+ or −2 wales). The thickness of this example is 0.024 inches.

In another embodiment the sling material may have one or more substances associated therewith through a process such as coating. Examples of appropriate substances include, without limitation, drugs, hormones, antibiotics, antimicrobial substances, dyes, silicone elastomers, polyurethanes, radiopaque filaments or substances, anti-bacterial substances, chemicals or agents, including any combinations thereof. The substances may be used to enhance treatment effects, reduce potential sling rejection by the body, reduce the chances of tissue erosion, enhance visualization, indicate proper sling orientation, resist infection or other effects. For example, the sling may be coated by the process described in U.S. Pat. Nos. 5,624,704; 5,756,145; 5,853,745; 5,902,283 and 6,162,487 (the entire contents of which are hereby incorporated by reference).

FIG. 1 illustrates a sling assembly comprising sling 42 and sheath 44 that are made of biocompatible materials having sufficient strength and structural integrity to withstand the various forces exerted upon these components during an implant procedure and/or following implantation within a patient.

Preferably, the overall dimensions of the sling assembly 46, including insertion sheath 44 and sling 42 are sufficient to extend from an abdominal incision, to an undersurface of the urethra and back to another abdominal incision with additional size to account for the imprecision associated with the range of human anatomy sizes. In a preferred embodiment, the sheath length of the assembly of the present invention is approximately within the range of 52.0 cm to 58.5 cm (20.5 inches to 23.0 inches), sheath width is approximately within the range of 1.0 cm to 1.63 cm (0.482 inch to 0.642 inch) and sheath material thickness is approximately within the range of 0.127 mm to 0.203 mm (0.005 inch to 0.008 inch), respectively. The associated sling 42 has a length, width and thickness approximately within the range of 40 cm to 51 cm (15.7 inches to 20.1 inches), 1.0 cm to 1.2 cm (0.394 inch to 0.472 inch) and 0.508 mm to 0.711 mm (0.020 inch to 0.028 inch), respectively.

The sling 42 of the present invention can be implanted without the need for bone screws. Upon implantation, a portion of the sling 42 is passed and/or woven through various layers of abdominal/pelvic tissue.

The sling 42 is designed to remain within the body of a patient as an implant for a predetermined therapeutically effective amount of time. The sling may be non-absorbable, absorbable or resorbable, including any combinations of these material properties, depending on the desired treatment. The general characteristics of the sling material and design should be such as to withstand the various forces exerted upon it during implantation (for example, frictional forces associated with tissue resistance) and after implantation (for example, increased abdominal or bladder pressure caused by a stress event).

The precise, final location of the sling 42 will depend on a variety of factors including the particular surgical procedure(s) performed, and any preconditions of the patient such as scar tissue or previous surgeries. For example, it may be preferred to place the sling 42 in close proximity to, but not in contact with, a mid portion of the urethra to treat incontinence.

According to one embodiment, the sling may include a protective sheath 44 (see FIG. 1). The sheath 44 is used during insertion of the strip 42. After the sling 42 is implanted, the sheath 44 is removed and discarded. Preferably, the protective sheath 44 is constructed of a material that affords visual examination of the implantable sling material 42 and that affords convenient passage of the assembly 46 through tissue of the patient.

In a preferred embodiment, the sheath 44 is made of polyethylene. Other materials including, without limitation, polypropylene, nylon, polyester or Teflon may also be used to construct the sheath 44. The sheath material should be flexible and provide sufficient structural integrity to withstand the various forces exerted on the sheath 44 throughout the sling delivery procedure. In general, the sheath 44 is configured to have sufficient flexibility to facilitate user manipulation and adequate structural strength to withstand the various forces applied to the sheath 44 during delivery and/or positioning of the sling assembly 46. It should also conveniently separate from the sling material 42 after the sling 42 is implanted without materially changing the position of the sling 42.

The sheath 44 may comprise two elongate, separable sections. Optionally, portions of the sheath 44 may detachably and telescopically overlap near the middle portion of the sling. In addition to resisting sling exposure and contamination, the overlapping section may also be used as a visual indicator for the practitioner or user of the device. Additionally, orientation indicia (not shown) may be placed on the overlapping portion to indicate proper orientation of the sling relative to the urethra. Alternatively, other configurations of the sheath 44 are within the scope of the present invention. In particular, the sheath may be unitary as opposed to telescoping with perforations, slits, holes, scores or tear lines designed to allow separation and removal of the sheath 44.

During sheath removal, the first section and the second section of the sheath are slid off the sling 42 by pulling each end of the sheath 44 away from the middle portion of the sling assembly 46. Removal of the sheath 44 causes separation of the overlapping sheath sections, thereby exposing the sling 42. In addition, the smooth outer surface of the sheath 44 provides a relatively frictionless surface to facilitate passage of the sheath 44 through the various tissues. The relatively frictionless motion also avoids disturbing the position of the sling 42 relative to the anatomy of the patient.

In another embodiment of the invention, the sheath 44, or a portion thereof, is associated with one or more substances including those substances identified with respect to sling 42. The substances may be used to enhance sheath removal, identify twists along the sheath 44 (and thereby indicate proper sling orientation), indicate cutting/separation points, indicate center-point, resist infection or provide other desirable effects. For example, a first surface of the sheath 44 may include indicia that should lie opposite the urethra or bladder neck to ensure proper sling orientation. Thus, the indicia provide the practitioner/surgeon with a visual indicator to aid in properly orienting the sling assembly 46, and ultimately the sling 42, within the patient.

In another aspect, the present invention comprises a coupler (e.g. 54, FIG. 1) for use in a surgical sling procedure. Referring to FIGS. 2 through 8, the coupler 54 comprises a body portion having first end portion 56 and second end portion 52 opposite the first end portion 56. The first end portion 56 has surfaces for receiving the insertion end of a needle (e.g. end 58 of needle 60). The coupler also includes an internal passageway with structure for connecting the needle 60 to the coupler 54.

Figure 16:
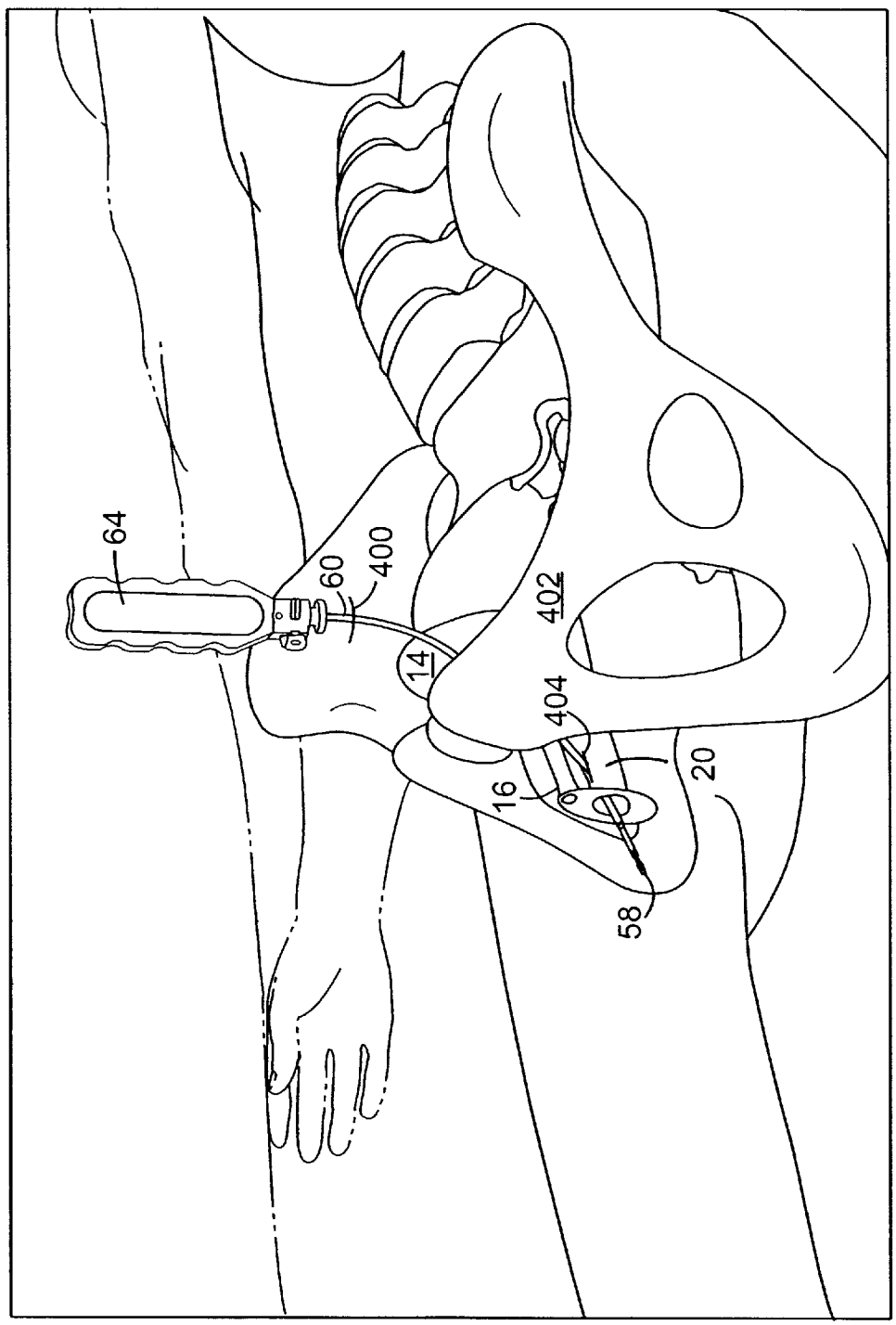

Referring to FIG. 16, the coupler 54 is attached to the insertion end 58 of needle 60 after the end 58 emerges from a vaginal incision 404. The connection between the needle 60 and the coupler 58 is accomplished quickly by pushing the coupler onto the end of the needle in a substantially axial fashion. As used herein, when it is said that the needle and coupler are moved together in a substantially axial fashion, it is meant that the motion is substantially linear with slight curvatures being with the scope of the invention. Preferably, the motion is substantially parallel with the axis of the coupler, taking into account that the coupler and/or needle may have a slightly curved axis. Connecting the needle and coupler in a substantially axial fashion, as opposed to articles that connect by being screwed together, is believed to be less distracting and more convenient for a surgeon. This motion is also believed to be less likely to cause the needle to deflect and damage tissue.

The force required to connect the coupler 54 to the needle 60 should be relatively small to avoid distracting the surgeon. By relatively small, it is meant that the force required to connect the needle and coupler should not unduly tax the strength of a majority of people.

Preferably, there is a tactile sensation when the coupler 54 is fully seated on the needle 60. The tactile sensation signals the surgeon that the needle 60 may be pulled upward through the body without separating from the coupler 54.

The second end portion 52 of the coupler 54 has sling association structure for associating the article with a sling or another needle (see FIG. 21). The sling association structure may comprise a hole 90 and a portion of internal passageway 96 near end 52.

Preferably, the coupler 54 comprises a dilator that dilates a track for ease of sling introduction and positioning within the patient. End 58 of the needle 60 is preferably keyed to allow for convenient, secure attachment of the needle 60 relative to the coupler 54. In a preferred embodiment, the key feature resists rotation of the coupler 54 relative to the needle 60.

The assembly preferably includes two couplers. The coupler 54 atraumatically creates and/or expands the passageway through the tissues for sling assembly delivery. The coupler 54 is preferably short relative to a needle 60 for ease of passage of the assembly and to reduce the overall amount of tissue that is deflected at one time. Preferably, the coupler is less than 2.5 inches in length, and more preferably, it is less than 1.5 inches in length. The maximum radius of a coupler 54 is preferably less than 10 mm, more preferably less than 7.5 mm, even more preferably less than 5 mm. The tip of the coupler 54 is preferably blunt, as, in preferred embodiments, the leading tip of the coupler 54 will pass through tissue that has already been pierced by a needle 60.

The coupler 54 may be made from a variety of biocompatible and sterilizable materials including, without limitation, acetal, polypropylene, Delrin™, Acrylonitrile-Butadiene-Styrene (ABS), polyethylene, nylon and any combination of biocompatible materials.

The coupler 54 preferably includes internal surfaces shaped in a predetermined fashion to engage or abut complementary surfaces on needle 60. In a preferred embodiment, the needle connector surfaces afford a permanent affixation between the coupler 54 and the needle 60. By "permanent affixation", it is meant that it would be very difficult to separate the coupler from the needle after they have become permanently affixed.

After implantation of the sling 42, to separate the sling 42 from the coupler 54 needle 60, the surgeon cuts an end of the sling 42 as described more fully below. The needle/coupler attachment surfaces preferably afford quick and convenient attachment of the coupler 54 to the needle 60 to avoid wasting time in the midst of a surgical procedure. In contrast to focusing on a tedious or difficult connection of an article protruding from the body and another article, with the present invention, the surgeon can rapidly and securely attach the needle 60 to coupler 54 simply by pushing the coupler 54 onto the needle 60 in a substantially axial (preferably linear) fashion. The attachment is secure to avoid separation of the needle 60 and coupler 54 while the combination is passed through tissue.

As seen in FIGS. 1 through 9, the first and second ends 58 and 62 of the needle 60 may include a keying feature affording secure association between the needle and coupler 54 and/or sheath assembly 46. In one embodiment, the keying feature comprises a recess 130 and/or square-shaped portion 126. As previously described, the recess 130 and square-shaped portion 126 are designed for complementary engagement to the appropriate end of coupler 54.

The coupler 54 also includes a universal sling association structure (e.g. hole 90) for associating with a sling. Preferably, the coupler 54 is preattached to the sling 42 and/or sheath 44 (or the combination thereof), particularly if the sling is a synthetic material.

Referring to the embodiment of coupler shown in FIGS. 2 through 8, the coupler 54 may be approximately 3.1 cm (1.2 inches) in length. The coupler 54 preferably includes a gentle taper 88 near its first end 56. The coupler is sized and shaped to provide atraumatic passage through body tissue. The taper 88 and relatively smooth outer surface of the coupler 54 facilitate atraumatic passage of the coupler 54 and attached sling assembly 46 through the various tissues of the patient. The presence of the coupler 54 preferably allows a gentle transition between the diameter of the needle, to the shape of the coupler, and finally to the sling assembly 46, as opposed to prior art assemblies, where the structure of the sling assembly abruptly increases the profile of the needle and thereby the size of the structure that must pass through tissue.

Preferably, the second end 52 of the coupler 54 associates the coupler with one end of a sling 42, or sheath 44 or sling assembly 46. The sheath 44 or sling 42 is preferably attached to the coupler 54 via a first opening or through-hole 90 located near the second end of the coupler 54. In this embodiment, the opening 90 could receive a variety of materials, such as fascia, autologous materials, synthetics, biologic tissues and any other similar tissues, including any combinations.

Figure 2:
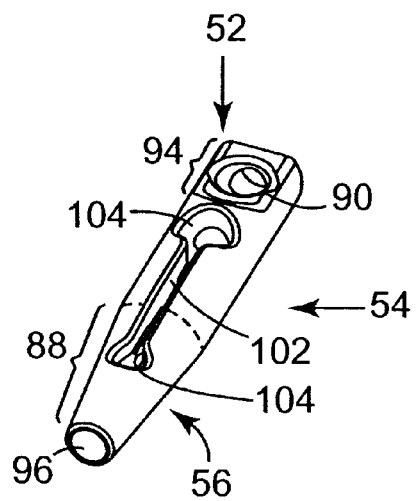
FIG. 2 is a perspective view of a coupler according to the present invention.
Figure 3:
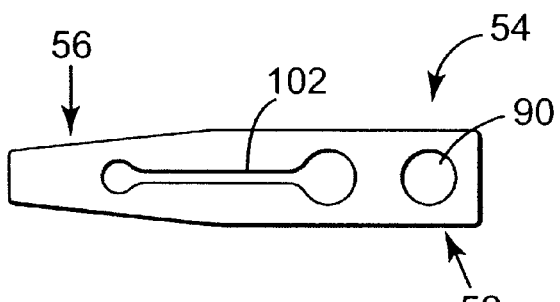
FIG. 3 is a top view of the coupler shown in FIG. 2.
Figure 4:
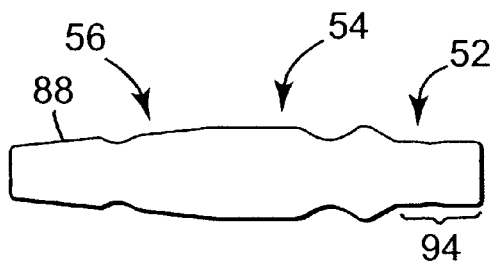
FIG. 4 is a side view of the coupler of FIG. 2.
Figure 5:
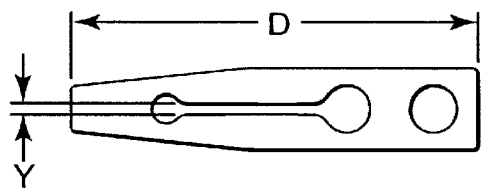
FIG. 5 is top view of the coupler shown in FIG. 2, similar to the view shown in FIG. 3, but showing different reference characters.
Figure 6:
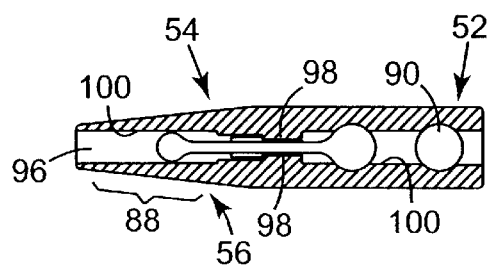
FIG. 6 is a sectional view of the coupler of FIG. 5.
Figure 7:
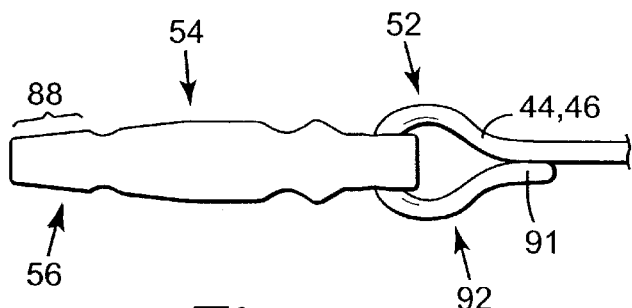
FIG. 7 is a side view of a coupler associated with a sling or a sling assembly.
Figure 8:
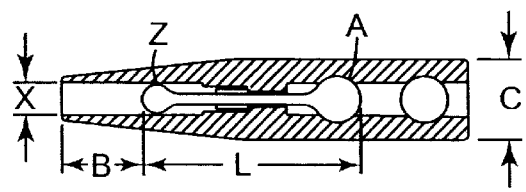
FIG. 8 is a sectional view of the coupler shown in FIG. 2, similar to the view shown in FIG. 6, but showing different reference characters.

In the embodiment shown in FIG. 1, the end portion 48 or 50 of one end of the sheath 44 is threaded through the opening 90 of the coupler 54 and secured to the sheath 44, thereby forming a loop. The edge portion 48 or 50 may be fastened onto the sheath 44 via ultrasonic welding, bonding, melting, suturing, sealing or other attachment techniques. Further, as shown in FIG. 2, the end 52 of the coupler 54 preferably includes a cut-away section 94 to provide room to receive sling assembly material to reduce the overall profile of the sling assembly experienced by tissue during sling passage. Therefore, when the sheath is attached to the cut-away section, the additional sheath material is not apt to significantly increase the relative thickness, diameter or profile of the coupler 54.

Alternatively, for couplers 54 manufactured via some molding techniques, the end of the sheath 44 may be encased within and secured to the second end 52 of the coupler 54 during the molding process. In yet another embodiment, the end of the sheath 44 may be fixedly attached within a longitudinal slot located near the first end 52 of the coupler 44 using an adhesive, ultrasonic welding or other attachment techniques.

Referring to FIGS. 2–6, the first end 56 of the coupler 54 includes a second opening or through-hole or lumen 96 that extends substantially internally along the longitudinal axis of the coupler 54. The hole 96 preferably extends the length of the coupler 54.

The lumen 96 has an internal diameter generally configured for convenient attachment to a needle 60 or similar sling-delivery device. In one embodiment, the internal diameter of the second opening 96 of the coupler 54 is approximately within the range of 0.239 cm to 0.3 1 8 cm (0.094 inch to 0.125 inch). A shoulder 98 located on the surface 100 of the second opening 96 of the coupler 54 and a complementary mating recess located on the surface of the first end of the needle 60 securely and permanently attach or lock the coupler 54 and needle 60 together. Once the needle 60 is inserted into the coupler 54, they are preferably not separated thereafter. After the sling 42 is implanted, the connected needle 60 and coupler 54 are removed from the sling by cutting an end of the sling as described in greater detail below. Preferable, the needle 60 and coupler 54 are discarded after the surgical procedure.

One or more longitudinal slots 102 located on the outer surface of the coupler 54 and in comununication with the second opening 96 allow the wall of the coupler 54 to expand in a radially outward direction when the first end of the needle 60 is inserted into the second opening 96 of the coupler 54. When the shoulder 98 of the coupler 54 passes the recess of the needle 60, the wall of the coupler 54 collapses around the needle 60 as the shoulder 98 seats into the recess, thereby securing the coupler 54 on the needle 60 and blocking separation of the coupler 54 and needle 60.

Although the invention has been described in terms of a shoulder 98 and mating recess, alternative coupler-needle attachment mechanisms such as bumps, grooves, slots, wedges, detents and other mechanisms are also included within the scope of the claimed invention.

The coupler 54 preferably includes one or more relief ports 104 to facilitate convenient needle connection. The relief ports 104 may be formed at the ends of the longitudinal slots 102 or at various high-resistance locations along the coupler 54. The relief ports 104 decrease the rigidity or resistance of radially outward expansion of the coupler wall and reduce the amount of force required to insert or securely attach the needle 60 to the coupler 54. The relief ports contribute to a desired reduction in the force required to insert the needle into the coupler 54. In yet another embodiment, superficial bands or rings, arc-shaped slots, superficial grooves or other mechanisms may provide improved expansion or attachment characteristics.

A portion of the coupler 54 includes a taper 88 having a decreasing profile toward the second end 56 of the coupler 54. The taper 88 preferably gently cams tissue out of the path of the sling assembly 46 as the sling assembly is inserted in the body. The taper 88 is also sized and shaped to reduce the amount of friction or resistance as the device is drawn through the tissues of the patient. The amount of force required to manipulate the device through the tissues is thereby reduced. This in turn provides the user of the assembly with additional control over device insertion and maneuverability through tissue and within the patient. In addition to tapered profiles, other coupler profiles such as conical, flared, frusto-conical, pyramid-shaped, elliptical or other applicable profiles may also be used. Overall, the profile of the coupler 54 is preferably configured to provide easy dilation of the tissue to accommodate smooth passage of the sling 42/sling assembly 46 and subsequent collapse of the surrounding tissue to securely anchor the sling 42 into the tissue (after sheath removal).

The assembly of the present invention optionally includes handles 64. The handles may have any of the structure and features described in U.S. patent application Ser. No. 09/917,443 filed Jul. 27, 2001 (the entire contents of which are herein incorporated by reference).

Instead of a hole 90 in the coupler 54, another mechanism may be utilized to connect a coupler 54 to a surgical sling material, sheath or sling assembly.

Other accessories may also optionally be included in a kit according to the present invention. For example, a surgical drape specifically designed for urological procedures such as a sling procedure may be included in a kit of the present invention. Such a drape is disclosed in U.S. patent appl. Ser. No. 09/749,254, filed Dec. 27, 2001 (the entire contents incorporated herein by reference). Alternatively, an article for objectively setting tension of the device, such as those described in U.S. patent application Ser. No. 09/968,239, filed Oct. 1, 2001 (the entire contents of which are incorporated by reference) may be included in the kit.

The kits according to the present invention preferably include at least two needles. Two or more needles reduce the need to reuse a needle at a different location with a patient, thereby eliminating cross contamination issues. Additional needles, handles, couplers and other elements may also be included for surgical convenience, for avoidance of contamination from one portion of the body to another, for ease of manufacturing or sterilization or for surgical requirements.

The individual elements of the kits of the present invention may be packaged together, separately or in subassemblies depending on a variety of factors such as shelf life and sterilization requirements. They may be assembled at the manufacturing location or at the healthcare location. Any suitable sterilization procedure may be utilized to sterilize the contents of a kit. Suitable sterilization techniques include, but are not limited to steam, ethylene oxide, electron beam, vapor (e.g. hydrogen peroxide or peracetic acid), or plasma procedures.

EXAMPLE 1

Needle/Coupler

Figure 10:
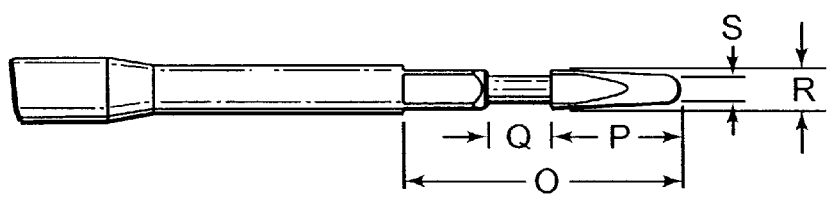
FIG. 10 is an end view of a needle according to the present invention.

A needle as shown in FIGS. 9 and 10 was constructed from 316 stainless steel. A coupler as shown in FIGS. 2 through 6 and 8 was injection molded from acetal (Texapol 5209). Table A lists some of the measurements of the various features.

TABLE A

| Reference Character in Figures | Length (inches) |
|---|---|
| D | 1.195 |
| Y | .031 |
| C | .235 |
| A | .139 |
| Z | .085 |
| X | .096 |
| B | .230 |
| L | .645 |
| N | 8.680 |
| O | .515 |
| P | 0.25 |
| Q | 0.13 |
| R | .094 |
| S | .060 |

Various additional construction details of the coupler and needle are disclosed in U.S. Provisional Patent Application No. 60/332,330, filed Nov. 20, 2001, entitled, "Sling Assembly Articles", Inventors: Gary Rochleau, Johann (Hans) Niesz and Gary Nachreiner.

EXAMPLE 2

Insertion/Separation Force

Figure 11:
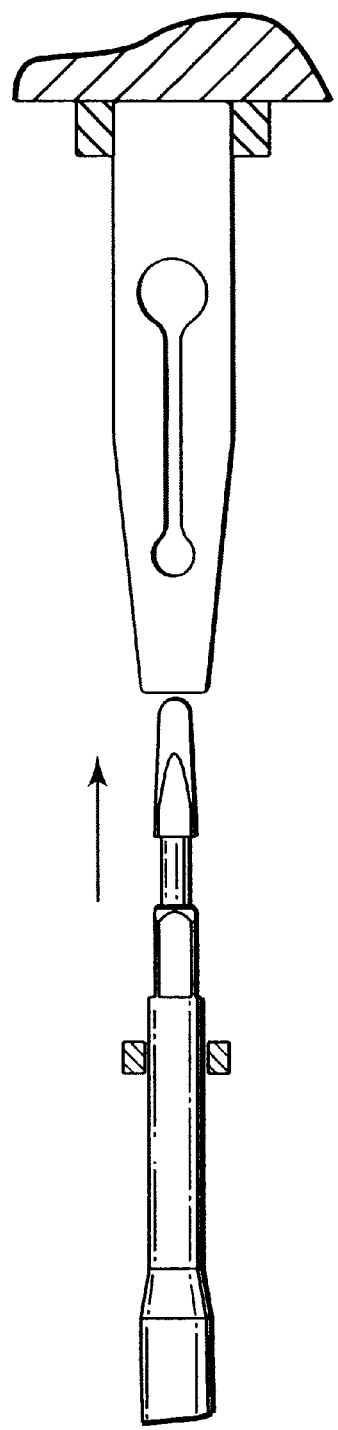

FIGS. 10 and 11 are schematic illustrations of test equipment used to record Separation Forces and Insertion Forces for a needle and couplers. Ten sterilized and aged couplers were provided in accordance with Example 1. A new coupler was used for each Insertion Force/Separation Force test. A single needle was constructed in accordance with Example 1. The needle was used for each Insertion Force/Separation Force test.

The test equipment included an Instron, 200 lb Load cell, Torque Meter device. To obtain the Insertion Force, the needle was loaded into the load cell in the Instron device. The coupler was loaded into a holding fixture (see FIG. 11). The fixture was clamped into the lower air grip of the Instron device. The needle was lowered down and inserted into the coupler to align the needle and coupler but not to induce a load. The needle was then inserted substantially in the direction of the arrow in FIG. 11 at a rate of 0.5 in/sec into the coupler until it locked onto the coupler. The Insertion Force was then recorded.

Figure 12:
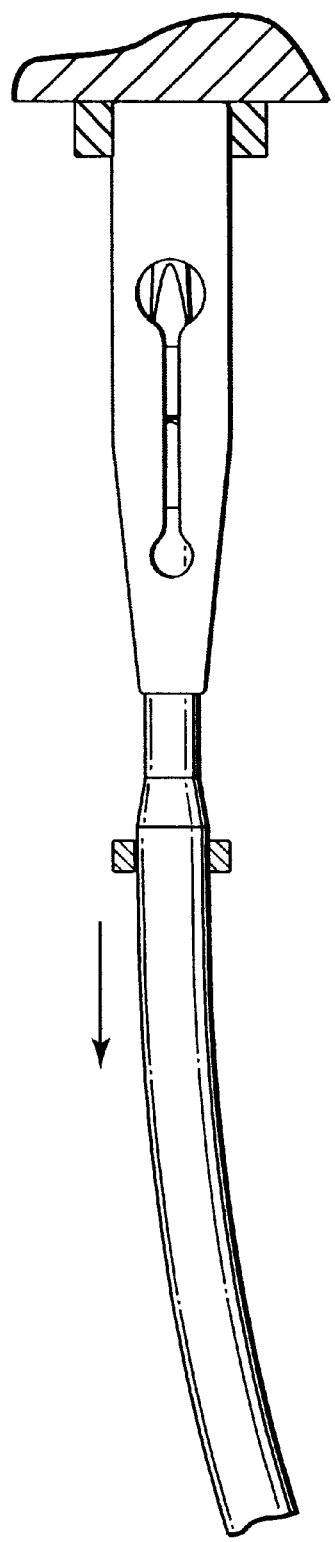

To obtain the Separation Force measurement, the needle was pulled out of the coupler in the direction of the arrow in FIG. 12 at a rate of 0.5 in/sec. The Separation Force was then recorded.

The data for the Separation Force and the Insertion Force is recorded in Table B.

TABLE B

| Needle/Coupler Insertion Force (lbs.) | Needle/Coupler Separation Force (lbs.) |
|---|---|
| 7.95 | 33.50 |
| 7.74 | 31.74 |
| 5.28 | 35.59 |
| 6.89 | 32.33 |
| 5.32 | 29.57 |
| 9.53 | 30.82 |
| 6.17 | 30.93 |
| 8.86 | 30.86 |
| 7.58 | 34.40 |
| 6.96 | 29.52 |

An analysis of the data of Table B is provided in Table C.

TABLE C

| | Needle Coupler Insertion Force (lbs.) | Needle Coupler Separation Force (lbs.) |
|---|---|---|
| Average | 7.229 | 31.926 |
| Standard | 1.400 | 2.025 |
| Minimum | 5.278 | 29.520 |
| Maximum | 9.530 | 35.590 |

The results show that the Insertion Force is sufficiently low to make the needle/coupler attachment easy and convenient for almost every user, regardless of the individual's strength. Additionally, the separation force is extremely high to resist undesired separation of the coupler and needle.

A cadaver study was also conducted to study the force required to pull a coupler through tissue. This was determined using a Chatillon force measurement device on a needle assembly and pulling the coupler through tissue. In this test, the force on the coupler was found to be 11 lbs. Additional tests in animal tissues supported the belief that the force on the coupler as it moves through tissue is between about 3 and about 12 pounds. As a result, the Separation Force of this example is within desired limits.

Examples of Surgical Procedures

Several methods are contemplated herein. Procedures that address problems other than incontinence (e.g. cystocele, enterocele or prolapse) are also contemplated alone or in conjunction with the present invention. Further, the term "urethra," with respect to sling positioning, is used for brevity and reader convenience. It should be noted that the present invention is particularly suitable for placing a sling in a therapeutically effective position. The method may be utilized to support a variety of structures at different anatomical locations. As such, the terms "target site," "bladder", "urethro-vesical juncture", "vaginal vault", "U-V juncture" and "bladder neck" are also included within the scope of the present invention.

The present invention includes surgical procedures that utilize the novel surgical instruments and articles described above. The present invention also includes improved surgical sling procedures.

The present invention preferably utilizes a suprapubic approach, at least initially. A suprapubic approach affords greater control over the end of a needle to avoid areas with sensitive vascular structures and the obturator nerves. Further the heightened control associated with a caudad passage is believed to avoid injury to bowel tissue.

Referring now to FIGS. 13 through 20, a preferred embodiment of surgical procedure is disclosed. Initially, the patient is placed under local, spinal or general anesthesia. A small transverse incision 404 is made in the anterior vaginal wall 20 of a female patient followed by a transurethral dissection. Two small transverse suprapubic abdominal stab incisions 400 are also made near the back of the pubic bone (e.g. each about 1 cm from the midline, or alternatively, one large incision may be made) to allow for needle entry. Optionally, two paraurethral dissections (incisions next to the urethra) lateral to the midline may be created to allow the surgeon's finger to meet the end 58 of the needle 60 during the procedure.

Figure 13:
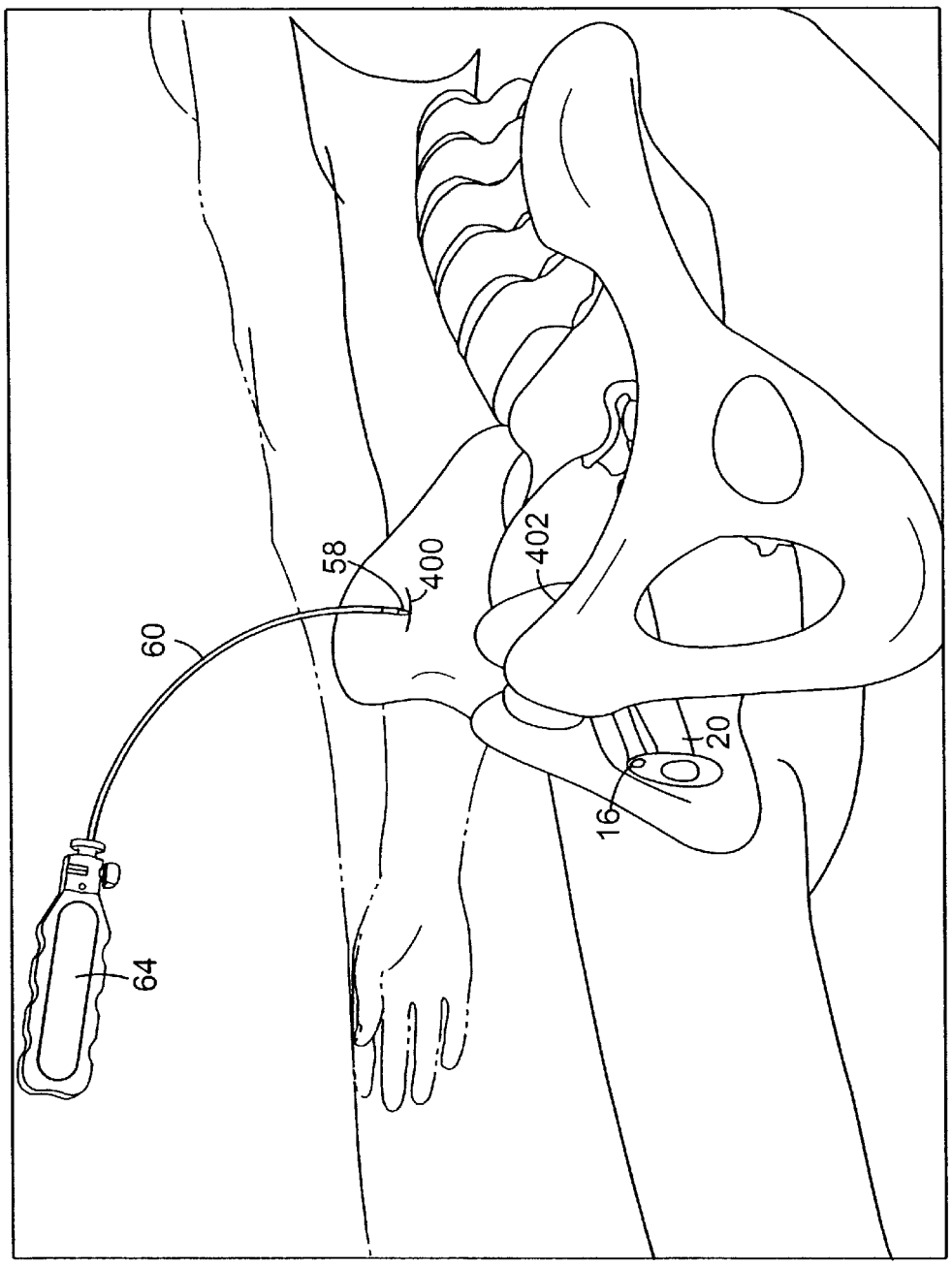

A handle 64 may optionally be used. Alternatively, the needle 60 can be used alone, without the handle 64. FIG. 13 shows the end 58 of needle 60 just passing an abdominal incision 400. Preferably, after the end 58 of the needle 60 passes the suprapubic abdominal incision 400, the surgeon seeks to encounter resistance associated with the posterior portion of the patient's pubic bone 402 with the end 58 of the needle 60 to controllably move the end 58 of the needle toward the vaginal incision 404 and to help avoid damaging structures such as the urethra and bladder of the patient. The end 58 of the needle 60 is used to identify the location of the pubic bone 402. The surgeon exploits the resistance provided by the pubic bone 402 to controllably pass the end of the needle 58. This approach is preferred as it helps keep the needle 60 away from major pelvic vessels, nerves and anatomical structures such as the urethra, bowels and bladder.

Figure 14:
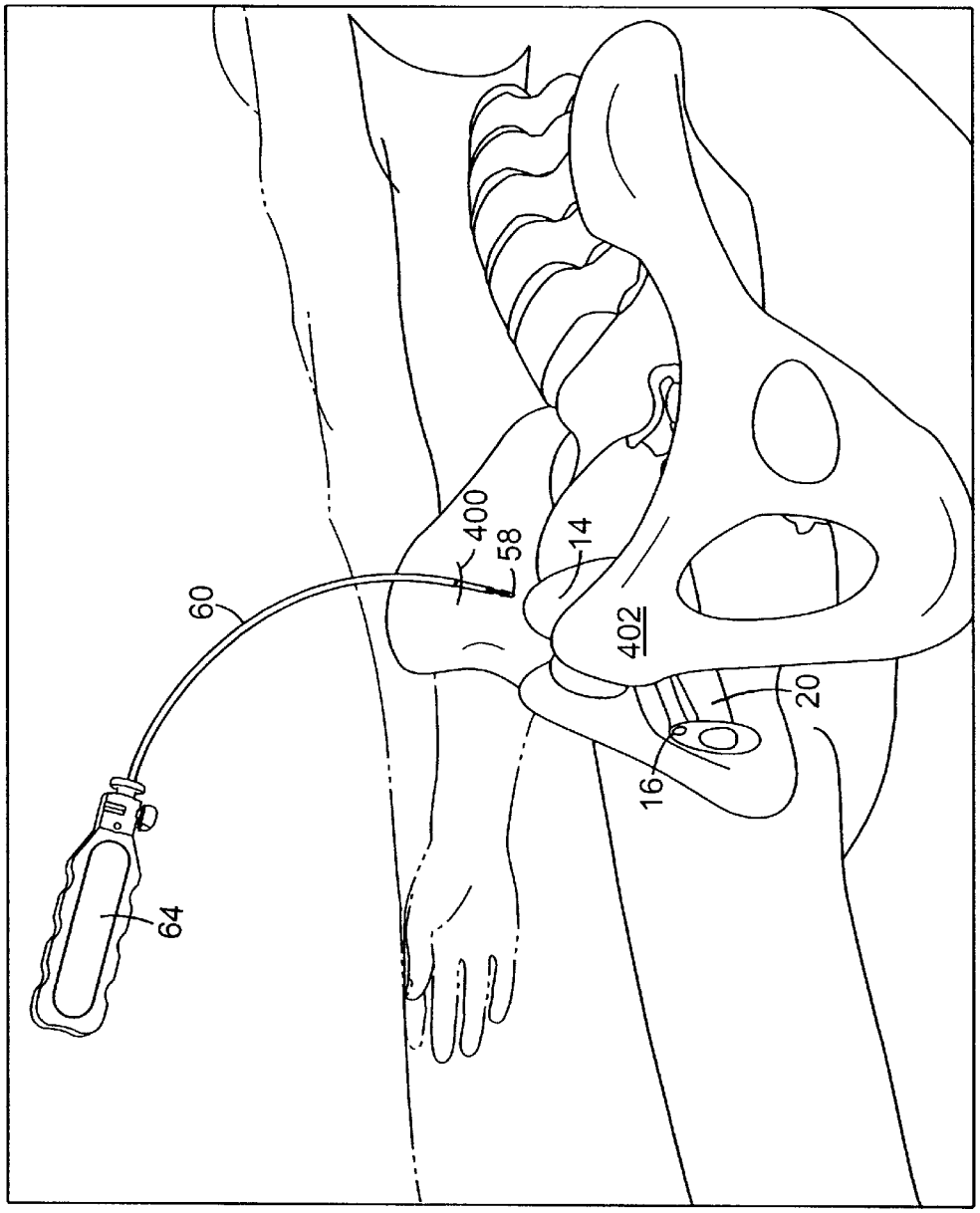
Figure 15:
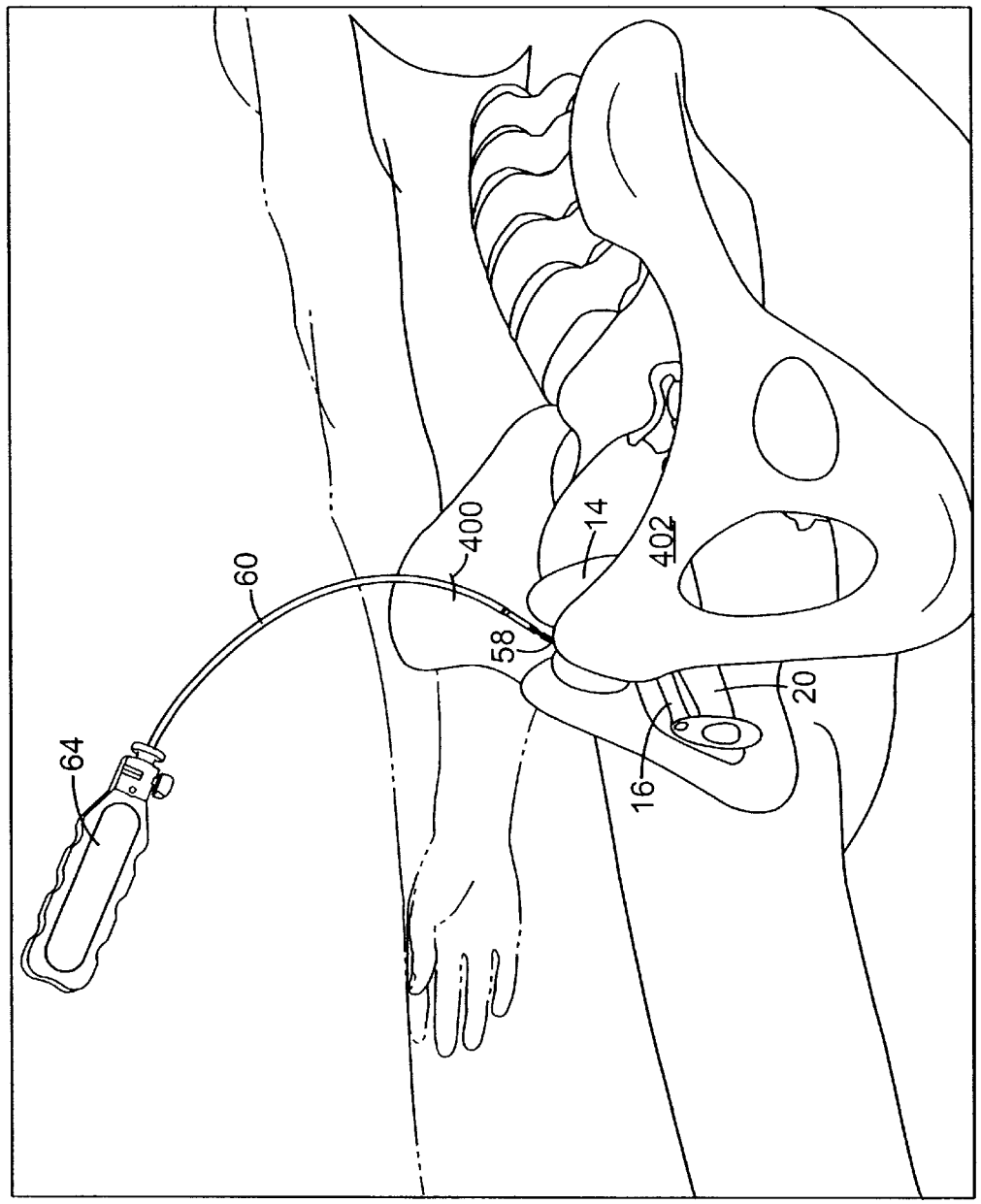

FIG. 14 illustrates the end of the needle as it just passes the suprapubic incision. FIG. 15 illustrates the needle 60 as the surgeon begins to experience the tactile feel of the resistance provided in part by the posterior portion of the pubic bone 402. FIG. 15 shows the needle 60 as it passes in proximity to the posterior surface of the pubic bone 402 which continues to operate as an anatomical guide for the surgeon as the needle end 58 approaches vaginal incision 404 (see FIG. 16).

FIG. 16 illustrates the needle as it passes out of a vaginal incision 404. Optionally, with the index finger of a hand, the surgeon may meet the end 58 of the needle via the paraurethral dissection. The surgeon's finger may be delicately placed adjacent endopelvic fascia of the patient and used to guide the needle 60 through the relatively tough endopelvic fascia and into the vaginal incision 404. This helps the surgeon keep away from structures such as the bladder, urethra and other sensitive tissue.

The small diameter and curvature of the needles 60 help to provide precise passage of the needles 60 to the vaginal incision 404. In addition, this needle configuration creates a minimally invasive pathway through tissue extending between the abdominal wall and pubic space, thereby reducing the risk of perforating the bowel and/or blood vessels and nerves located lateral to the bladder 14.

The steps described above are preferably repeated as needed for a second needle 60 on the other side of the urethra 16. Once both needles are placed, surgeons typically perform a cystoscopy to ensure that the bladder is not punctured before implanting the sling. A cystoscopy confirms the integrity of the bladder 14 and urethra 16 or recognizes a bladder perforation.

Figure 17:
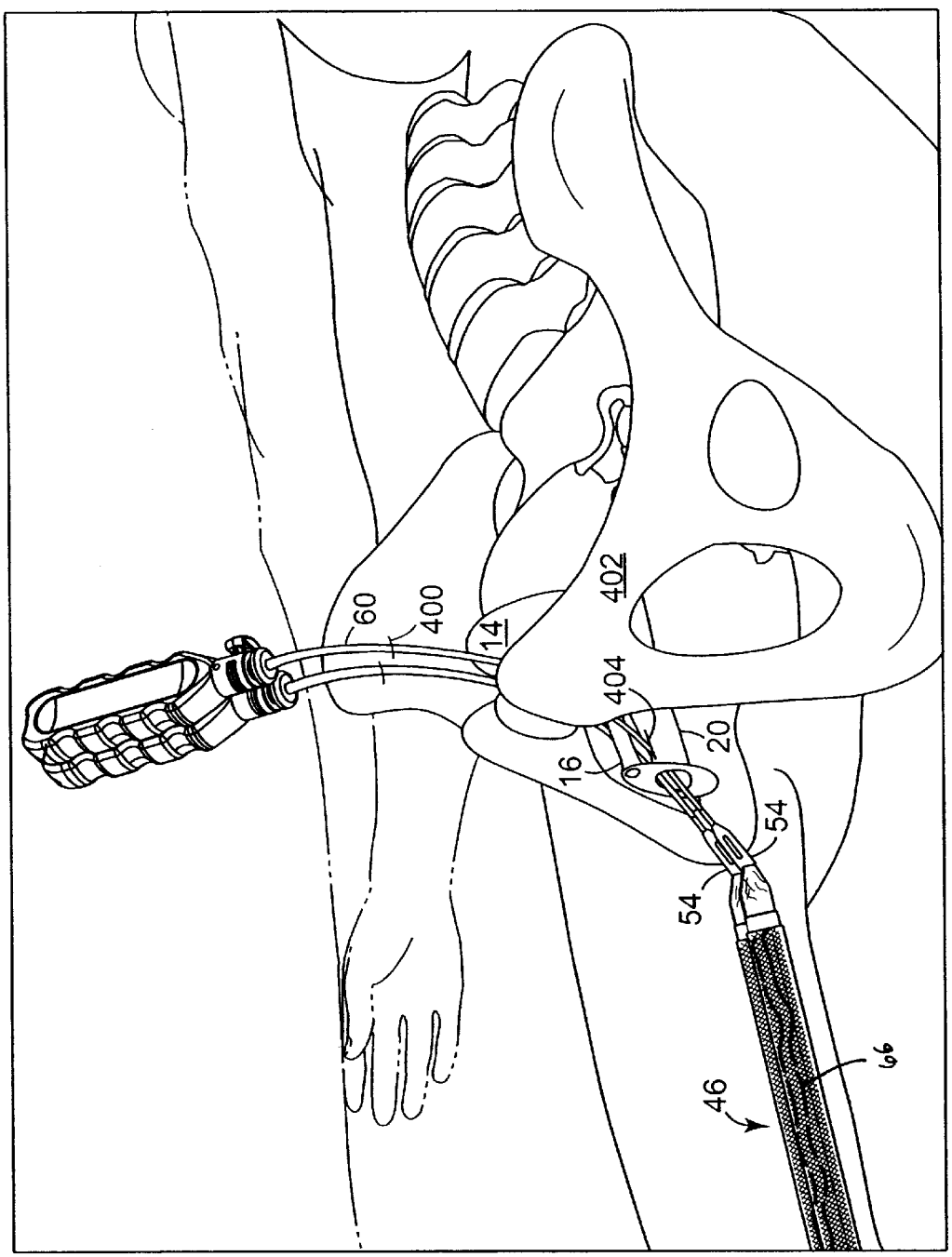

FIG. 17 is a perspective view of a sling associated with two needles 60. Adapters (e.g. couplers 54) are pushed onto the ends 58 of needles 60 as shown in FIG. 17. The couplers 54 are preferably snapped irreversibly into place for a secure connection. Next, if a synthetic sling assembly (such as the sling assembly of FIG. 1) is used, the plastic sheath 44 is oriented so that the optional center orientation indicia (e.g. a blue mark) is facing away from the surgical field, toward the surgeon After the couplers 54 are attached to the needles 60, the sling assembly 46 is properly oriented so that the sling assembly 46 is not twisted when attached to the couplers 54. Once the couplers 54 are securely attached, the needles are pulled up through the suprapubic incisions, taking care to avoid contact with sensitive tissue. The sling is then clamped with surgical clamps (not shown). During this portion of the process, the attached couplers 54 and sling assembly 46 are atraumatically pulled up through the needle paths, advancing the sling assembly 46 adjacent to and looped beneath the urethra 16 or target site. A portion of each end of the sling assembly 46 extending beyond the suprapubic incisions 400 is clamped and then cut to release the needles 60 and attached couplers 54.

The sling is placed in a therapeutically effective position. The precise anatomical position will depend upon a variety of factors including the type and degree of anatomical damage or insufficiency, whether the sling procedure is combined with other procedures and other surgeon decisions. Typically, the sling is placed midurethra, without tension, but in position to support the midurethra. Alternatively, the sling could be placed to support the bladder neck and/or UV junction.

Once the sling assembly 46 is carefully positioned under the midurethra or target site to provide sufficient support to the target site, the overlapping portion of the sheath 44 located near the center of the sling assembly 46 and optional member 66 (i.e. tensioning filament) may then be used to center and properly position the sling assembly 46 under the midurethra. The sheath 44 is then removed.

Figure 18:
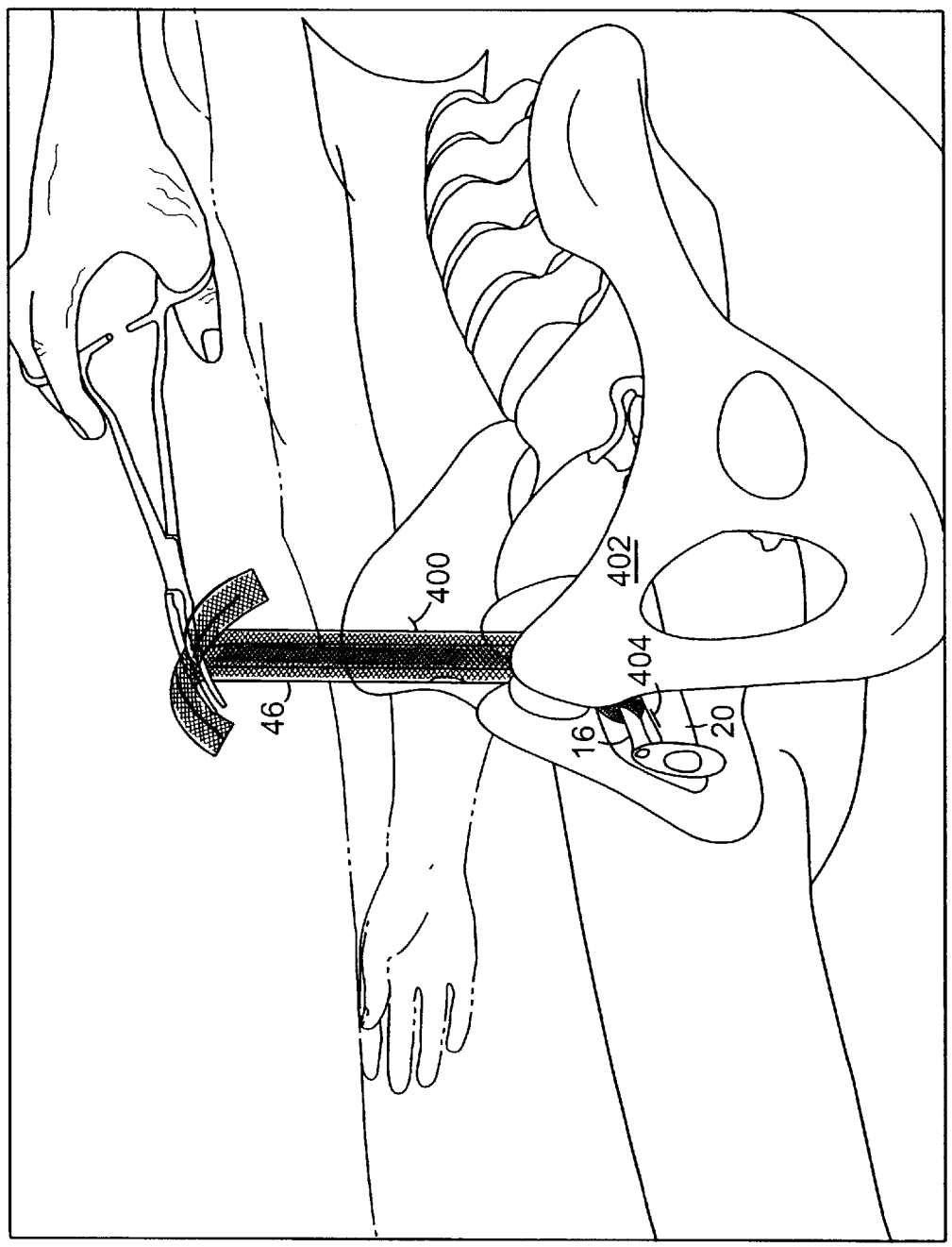
FIG. 18 is a perspective view of a sling being pulled upward in accordance with the present invention.
Figure 19:
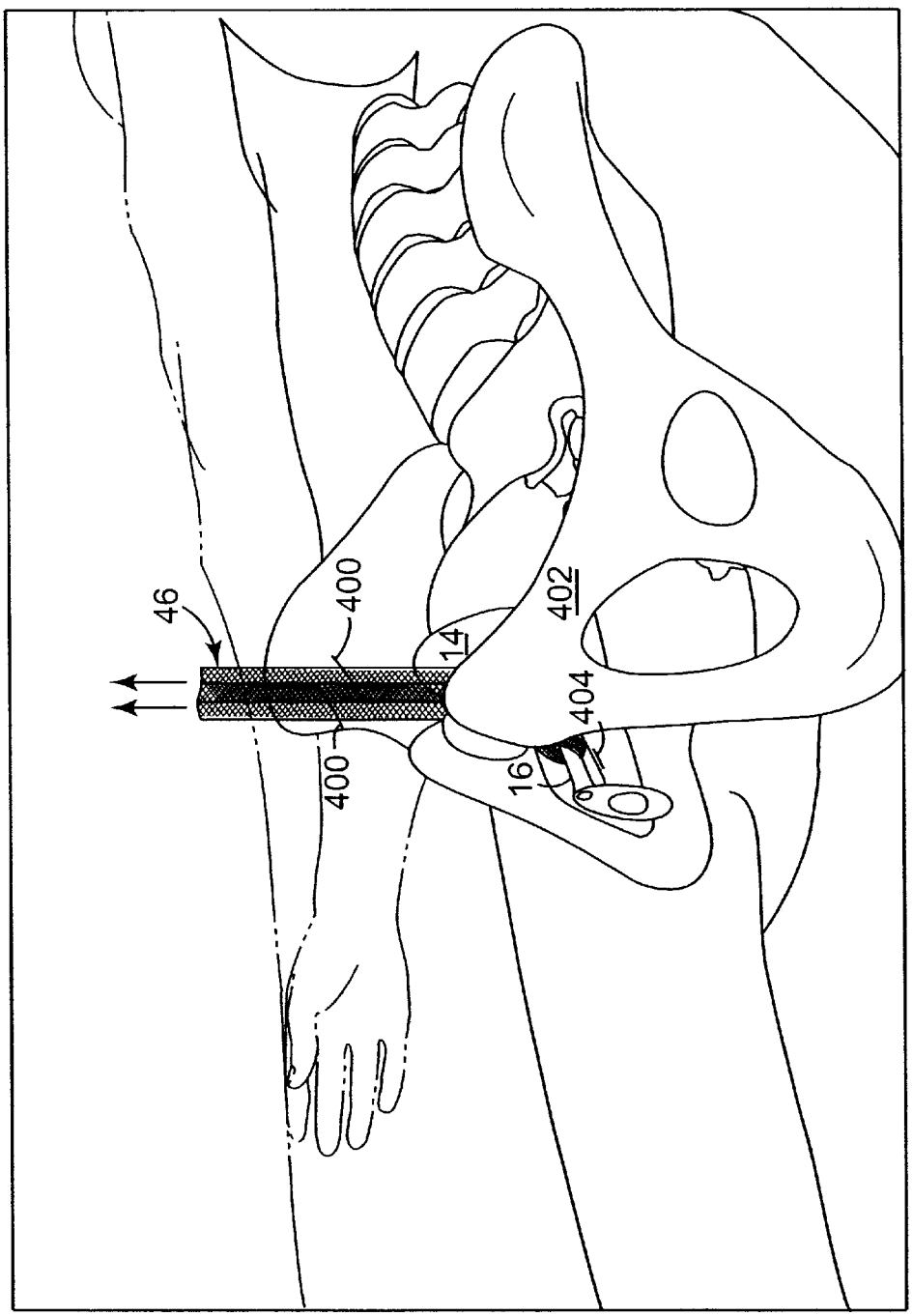
FIG. 19 is a perspective view of the sling according to the present invention after the couplers have been separated from the rest of the assembly, but prior to final trimming.
Figure 20:
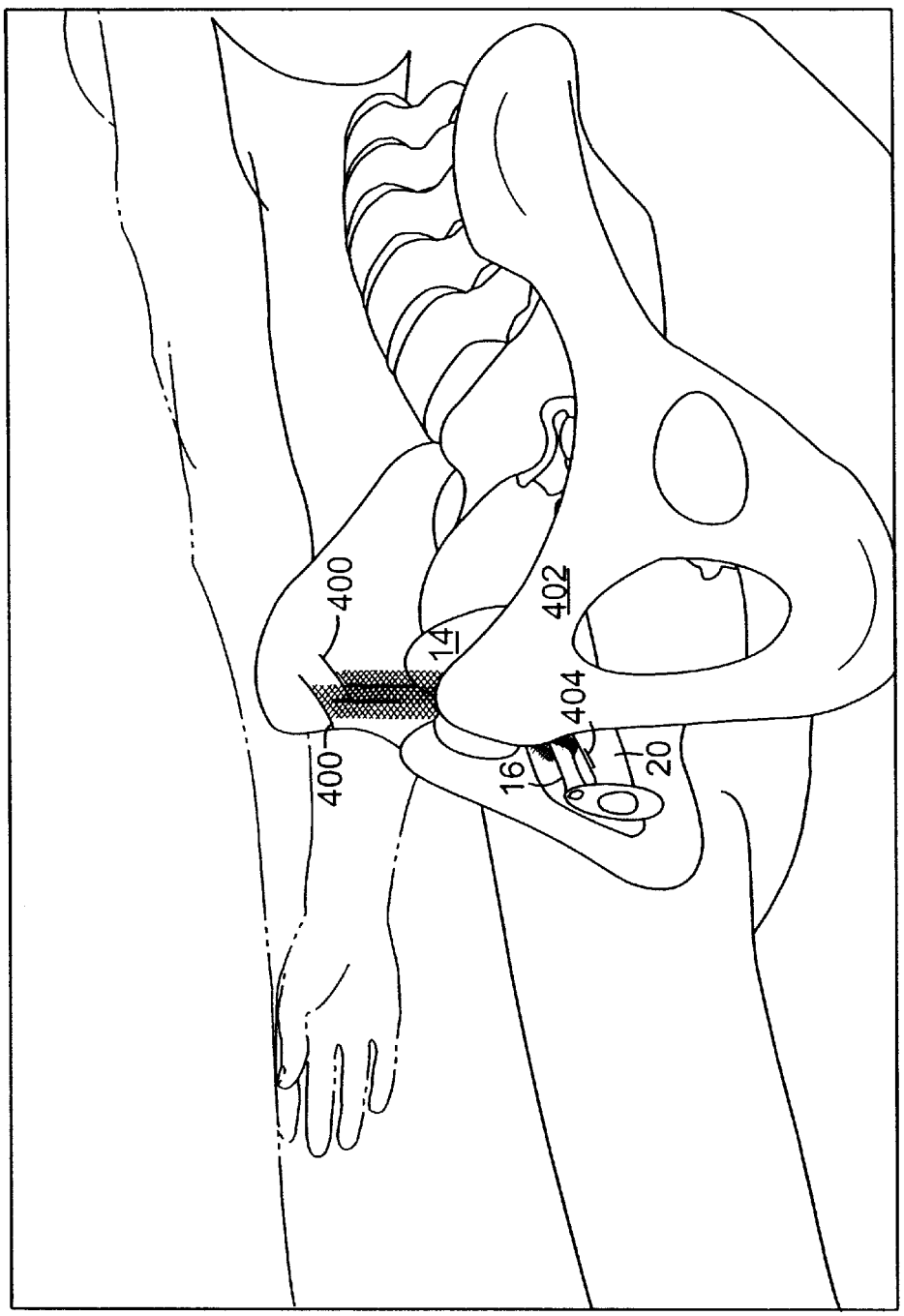
FIG. 20 is a perspective view of the sling according to the present invention after the sheath has been removed and the sling has been trimmed.

FIG. 18 shows the sling being tightened during the surgical procedure. Sling tension may be tightened by placing a device, such as a clamp, across one or both ends of the sling 42, suprapubically. Generally, the surgeon grasps the mesh adjacent the suprapubic incision 400 and pulls upward to increase the degree of tightness of the mesh. FIG. 18 shows the sling after the couplers have been cut off, but prior to final trimming.

After the couplers 54 are trimmed off, the plastic sheath 44 is removed from the sling mesh 42 by pulling up on both sides of the sheath 44, preferably one at a time. Optionally, to avoid overtightening the sling mesh 42 while removing the sheath 44, a forceps or other blunt instrument may be placed between the sling and the urethra. The forceps or other blunt instrument may be used to help establish a tension free aspect of the sling.

In another embodiment of the invention, shown with reference to FIG. 21, a method includes the steps of: providing at least one suprapubic or abdominal needle 602 with a relatively small diameter (e.g. less than 4 mm), and at least one sling associated needle 604, a sling 610 attached to the sling associated needle 604, and an adapter (e.g. coupler 54) having sling associated needle receiving surfaces (e.g. an end of innerpassageway 96 near the end of the coupler having hole 90) for receiving the end of the sling associated needle 604. For example, the sling associated needle 604 and sling 610 may comprise a TVT needle and sling available from Ethicon of New Jersey.

The method includes the steps of creating at least one vaginal incision 404, reating at least one suprapubic incision 400, and initially passing the suprapubic needle 602 through the suprapubic incision 400 and then through the vaginal incision 404, and connecting the adapter 54 to the needle 602 in a substantially axial fashion.

After being attached to a coupler, needles 604 are initially passed through vaginal incision 404 and toward one of the suprapubic incisions 400. While inserting the needles 604 initially through the vagina is not preferred, it is within the scope of the present invention, as some surgeons may prefer this approach due to previous surgical training, custom or personal preference. The method includes the step of placing the end of the sling associated needle 604 in an end of the coupler 54, and then moving the sling associated needle 604 from the vaginal incision 404 to the suprapubic incision 400 with at least the guidance of the suprapubic needle 602 to implant the sling 610. Handle 620 may be connected to a sling attachment end of needle 604 for this purpose. Guiding the end of the large sling associated needle 604 in this fashion is believed to help avoid contact between the sharp tip of needle 604 and sensitive structures such as obturator nerves, and vascular structures such as the superficial epigastric vessel, the inferior epigastric vessel, the external iliac artery and the obturator. Optionally, the coupler and sling associated needle 604 may include complementary engagement surfaces for securely attaching the needle 604 to the coupler 54 (and hence to the needle 602).

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An assembly for treating incontinence comprising: an elongate needle that is sized and shaped to be initially inserted through an abdominal incision and to then merge from a vaginal incision, the needle having an insertion end and an end opposite the insertion end, a sling for implantation in the body during an incontinence procedure, and a coupler having an axis, the coupler having a first end and a second end with surfaces for conveniently and securely connecting the coupler to the insertion end of the needle by moving the coupler and insertion end of the needle together, wherein the coupler is connected to the needle by being moved together in a substantially axial fashion.

2. An assembly according to claim 1 wherein after the needle is connected to the coupler, the assembly ha a Separation Force of at least about thirty pounds.

3. An assembly according to claim 1 wherein, the assembly has an Insertion Force of no more that about fifteen pounds.

4. An assembly according to claim 3 wherein, the assembly has an Insertion Force of no more than about ten pounds.

5. An assembly according to claim 4 wherein, the assembly has an Insertion Force of no more than about eight pounds.

6. An assembly according to claim 1 wherein the coupler is sized and shaped to be connected to the needle after the insertion end of the needle emerges from the vaginal incision.

7. An assembly according to claim 1 wherein the sling includes an insertion sheath and the first end of the coupler is attached to the sheath.

8. An assembly according to claim 1 wherein the tip of the insertion end of the needle is sub stantially blunt.

9. A coupler for use in an incontinence procedure that utilizes a sling and an elongate needle that is sized and shaped to be initially inserted through an abdominal incision and to then emerge from a vaginal incision, the needle having an insertion end, the coupler comprising
    an elongate body having an axis,
    a first end and a second end, and
    surfaces for conveniently and securely connecting the coupler to the insertion end of the needle by moving the second end of the coupler and the insertion end of the needle together in a substantially axial fashion.

10. A coupler according to claim 9 wherein the Insertion Force to connect the needle to the coupler is no more than about fifteen pounds.

11. A coupler according to claim 9 wherein the coupler includes an internal passageway for receiving the insertion end of the needle,
    the internal passageway having a shoulder portion that is sized and shaped to at least abut a complementary structure in a recessed portion of the needle to resist separation of the needle and coupler.

12. A coupler according to claim 9 wherein the first end of the coupler is adapted to be associated with a sling.

13. A method of treating incontinence in a female patient comprising the steps of:
    providing a synthetic surgical mesh having first and second ends and a plurality of holes that are sized and shaped to afford tissue ingrowth, and a removable synthetic insertion sheath associated with the surgical mesh,
    providing a needle that is sized and shaped to be initially inserted through a suprapubic incision and to then emerge from a vaginal incision, the needle having an insertion end and an end opposite the insertion end,
    providing a coupler having an axis, the coupler having a first end and a second end with surfaces for conveniently and securely connecting the coupler to the insertion end of the needle,
    creating at least one vaginal incision,
    creating at least one suprapubic incision,
    passing the leading end of the needle initially through the suprapubic incision and then through the vaginal incision,
    then connecting the coupler to the needle by moving the coupler and insertion end of the needle together while the insertion end of the needle protrudes from the vaginal incision,
    implanting the sling by moving the leading end of the needle from the vaginal incision toward the suprapubic incision, and
    then removing the synthetic insertion sheath.

14. A method according to claim 13 wherein the step of connecting the coupler to the needle by moving the coupler and insertion end of the needle includes the step of:
    pushing the coupler onto the insertion end of the needle together in a substantially axial fashion with an Insertion Force of less than about fifteen pounds.

15. A method according to claim 13 further including the step of connecting the first end of the coupler to a second needle that is attached to the surgical mesh and insertion sheath.

* * * * *